United States Patent
Diep et al.

(10) Patent No.: US 10,781,236 B2
(45) Date of Patent: Sep. 22, 2020

(54) BACTERIOCIN COMPOSITION AND METHOD

(71) Applicant: NORWEGIAN UNIVERSITY OF LIFE SCIENCES, Aas (NO)

(72) Inventors: Dzung Diep, Aas (NO); Ingolf Nes, Aas (NO); Ibrahim Mehmeti, Aas (NO); Ochinnikov Kiril, Aas (NO)

(73) Assignee: NORWEGIAN UNIVERSITY OF LIFE SCIENCES, Aas (NO)

( * ) Notice: Subject to any disclaimer, the term of this patent is extended or adjusted under 35 U.S.C. 154(b) by 0 days.

(21) Appl. No.: 15/777,009

(22) PCT Filed: Nov. 11, 2016

(86) PCT No.: PCT/EP2016/077497
§ 371 (c)(1),
(2) Date: May 17, 2018

(87) PCT Pub. No.: WO2017/084985
PCT Pub. Date: May 26, 2017

(65) Prior Publication Data
US 2018/0346524 A1 Dec. 6, 2018

(30) Foreign Application Priority Data
Nov. 17, 2015 (GB) .................................. 1520255.9

(51) Int. Cl.
| C07K 14/195 | (2006.01) |
| A61K 38/00 | (2006.01) |
| A23L 3/3571 | (2006.01) |
| A23L 3/3526 | (2006.01) |
| A23L 3/3463 | (2006.01) |
| A61K 38/16 | (2006.01) |

(52) U.S. Cl.
CPC ........ *C07K 14/195* (2013.01); *A23L 3/34635* (2013.01); *A23L 3/3526* (2013.01); *A23L 3/3571* (2013.01); *A61K 38/164* (2013.01); *A23V 2002/00* (2013.01); *A61K 38/00* (2013.01)

(58) Field of Classification Search
None
See application file for complete search history.

(56) References Cited

FOREIGN PATENT DOCUMENTS

WO    2011/073663    6/2011

OTHER PUBLICATIONS

Houghten et al. (Vaccines, Edited by Fred Brown: Cold Spring Harbor Laboratory) (Year: 1986).*
UK Search Report issued in UK Appln. No. GB1520255.9 dated Aug. 26, 2016.
NCBI Accession No. AHDX01000055.1, dated Aug. 15, 2012 (http://www.ncbi.nlm.nih.gov/nuccore/401152399).
NCBI Accession No. AHFF01000058.1, dated Aug. 15, 2012 (http://www.ncbi.nlm.nih.gov/nuccore/401249060).
NCBI Accession No. AHCQ010000123.1, dated May 16, 2013 (http://www.ncbi.nlm.nih.gov/nuccore/ahcq01000123.1).
Netz et al., Biochemical characterisation and genetic analysis of Aureocin A53, a new, atypical bacteriocin from *Staphylococcus aureus*, 2002, J. Mol. Biol. 319:745-756.
Tosukhowong et al., Garvieacin Q, a novel class II bacteriocin from *Lactococcus garvieae* BCC 43578, 2012, Appl. Environ. Microbiol., 78:1619-1623.
Villani et al., Detection and characterization of a bacteriocin, garviecin L1-5, produced by *Lactococcus garvieae* isolated from raw cow's milk, 2001, J. Applied Microbiol. 90:430-439.
Gabrielsen et al., Functional Genetic Analysis of the GarML Gene Cluster in *Lactococcus garvieae* DCC43 Gives New Insight into Circular Bacteriocin Biosynthesis, 2014, J. Bacteriol. 196:911-919.
Gabrielsen et al., The Maltose ABC Transporter in *Lactococcus lacti* Facilitates High-Level Sensitivity to the Circular Bacteriocin Garvicin ML, 2012, Antimicrobial Agents Chemother. 56:2908-2915.
AlKhatib et al., Lantibiotic Immunity: Inhibition of Nisin Mediated Pore Formation by NisI, 2014, Plos One 9:e102246.
Cotter et al., Bacteriocins: Developing Innate Immunity for Food, 2005, Nature Reviews Microbiology, 3:777-788.
Diep and Nes, Ribosomally Synthesized Antibacterial Peptides in Gram Positive Bacteria, 2002, Current Drug Targets, 3:107-122.
Sanchez et al., Antimicrobial and safety aspects, and biotechnological potential of bacteriocinogenic enterococci isolated from mallard ducks (*Anas plalyrhynchos*), 2007, Int. J. Food Microbiol., 117:295-305.
International Search Report and Written Opinion of the International Searching Authority, dated Apr. 6, 2017 in corresponding International Patent Application No. PCT/EP2016/077497.
Van der Auwera et al., "Whole-Genome Sequences of 94 Environmental Isolates of *Bacillus cereus* Sensu Lato", Genome Announcements, 1(5): e00380-13 (2013).
UniParc Database Accession No. UPI000279467D, amino acid sequence, XP-002766698, Oct. 31, 2012.
UniParc Database Accession No. UPI000279467C, amino acid sequence, XP-002766699, Oct. 31, 2012.
UniParc Database Accession No. UPI000279467B, amino acid sequence, XP-002766700, Oct. 31, 2012.

(Continued)

*Primary Examiner* — Padmavathi Baskar
(74) *Attorney, Agent, or Firm* — Wenderoth, Lind & Ponack, L.L.P.

(57) ABSTRACT

The present invention provides a multi-peptide composition with antibacterial activity comprising at least 3 peptides with the sequences as set forth in SEQ ID NO:1, 2 or 3 (or related sequences), respectively, in which the SEQ ID NO:1 sequence (or its related sequence) comprises at least two tryptophan residues. In particular the invention provides a new bacteriocin, Garvicin KS. The invention also provides compositions and host cells containing such antibacterial compositions. Uses of the antibacterial composition in treating bacterial infection and products treated with the antibacterial composition are also provided.

20 Claims, 13 Drawing Sheets
Specification includes a Sequence Listing.

(56) References Cited

OTHER PUBLICATIONS

Netz et al., "Molecular Characterisation of Aureocin A70, a Multi-peptide Bacteriocin Isolated from *Staphylococcus aureus*", J. Mol. Biol., 311(5): 939-949, (2001).

Coelho et al., "Immunity to the *Staphylococcus aureus* leaderless four-peptide bacteriocin aureocin A70 is conferred by AurI, an integral membrane protein", Research in Microbiology, 165(1): 50-59 (2014).

Ovchinnikov et al., "Novel Group of Leaderless Multipeptide Bacteriocins from Gram-Positive Bacteria", Applied Environmental Microbiology, 82(17): 5216-5224 (2016).

Senbagam et al., "Physical chemical and biological characterization of a new bacteriocin produced by *Bacillus cereus* NS02", Asian Pacific Journal of Tropical Medicine: 934-941 (2013).

Gao et al., "Garviecin LG34, a novel bacteriocin produced by *Lactococcus garvieae* isolated from traditional Chinese fermented cucumber", Food Control, vol. 50: 896-900 (2015).

Maldonado-Barragan et. al., "Garvicin A, a Novel Class IId Bacteriocin from *Lactococcus garvieae* That Inhibits Septum Formation in *L. garvieae* Strains", Applied and Environmental Microbiology, 79(14): 4336-4346 (2013).

Borrero et al., "Characterization of Garvicin ML, a Novel Circular Bacteriocin Produced by *Lactococcus garvieae* DCC43, Isolated from Mallard Ducks (*Anas platyrhynchos*)", Applied and Environmental Microbiology, 77(1): 369-373 (2010).

Office Action dated Mar. 26, 2020 in European Patent Application No. 16 795 317.3.

Morita et al., "Complete Genome Sequence and Comparative Analysis of the Fish Pathogen *Lactococcus garvieae*," PLoS One, Aug. 2011, vol. 6, Issue 8, pp. 1-8.

Ferrario et al., "Genetic investigation within *Lactococcus garvieae* revealed two genomic lineages," FEMS Microbial Lett, 2012, vol. 332, pp. 153-161.

Ferrario et al., "*Lactococcus garvieae*: Where Is It From? A First Approach to Explore the Evolutionary History of This Emerging Pathogen," Plos One, Dec. 2013, vol. 8, Issue 12, pp. 1-11.

\* cited by examiner

Figure 5A

```
MGAIIKAGAKIVGKGVLGGGASWLGNNVGEKINN    GarKosA    3453.15    10.8
MGAIIKAGAKIGKGLIGGAAGGAPYGGLKKIFG    GarKosB    3160.85    10.9
MGAIIKAGAKIVGKGAIWGGGVWLAEKLFGGK---  GarKosC    3099.77    10.8
********,**** * * *..                           Mr, Da      pI
```

Figure 6

```
GarvicinKosA    MGAIIKAGAKIVGKGVLGGGASWLGWNVGEKIWK
GarvicinKosB    MGAIIKAGAKIIGKGLLGGAAGGATYGGLKKIFG
GarvicinKosC    MGAIIKAGAKIVGKGALTGGGVWLAEKLFGGK CereinHA        MAKIGKWVVKGAAGYLGWEIGEGIWK
CereinHB        MGALVKGGLKLIGGTAASWLGWEAGERVWK
CereinHC        MGAIIKGGLKLVGGGAAGGPTYGGLKKIFG
CereinHD        MGAIIKGAAKVLGKGAATGGVIYGLEKLFR CereinVA        MGAVVKGALKIIGGGAASGGAVYGLERIFGR
CereinVB        MGAAVKMLGKAFAGGVAGGATYGGLKKIFG
CereinVC        MGAVVKGGLKIIGGTAASWLGWEAGTRIWK CereinX A       MGKKIGKWIITGAAGWAGWEIGEGIWK
CereinX B       MKYLGTLIKGAAGGAGAYVGEKIYNWYKN
CereinX C       MGALFKAALKAAGGGAAGGATYGGLKHFFG A70A            MGKLAIKAGKIIGGGIASALGWAAGEKAVGK
A70B            MGAVAKFLGKAALGGAAGGATYAGLKKIFG
A70C            MGALIKTGAKIIGSGAAGGLGTYIGHKILGK
A70D            MGAVIKVGAKVIGWGAASGAGLYGLEKIILKK
```

BACTERIOCIN COMPOSITION AND METHOD

The present invention relates to a bacteriocin which is a multi-peptide composition comprising at least three peptides as defined herein. The bacteriocin is a broad spectrum antibacterial agent with superior activity and may be used to treat a variety of bacterial infections, particularly drug-resistant strains of bacteria.

Resistance of bacterial pathogens to antibiotics and other antimicrobial drugs has become a well-recognized problem. Notwithstanding the recognition of this problem, only two new classes of antibiotics: oxazolidinones (linezolid) and cyclic lipopeptides (daptomycin) have reached the market in the last three decades and neither of these drugs has a novel mechanism of action and the development of resistance may be expected. There is an urgent need for new antimicrobial agents and new strategies to overcome multidrug-resistant bacteria.

One alternative to antibiotics is antibacterial peptides (bacteriocins), which can be used in both the food industry and in medicine (Cotter et al., 2013, Nature Reviews. Microbiology, 11, p 95-105; Cleveland et al., 2001, Int. J. Food Microbiol., 71, p 1-20; O'Sullivan et al., 2002, Biochimie, 84, p 593-604).

Bacteriocins are ribosomally synthesized antimicrobial peptides produced by many different bacteria (Cotter et al., 2005, Nature Reviews Microbiology, 3, p 777-788; Diep and Nes, 2002, Current Drug Targets, 3, p 107-122). Their antimicrobial activity is generally targeting only towards species/genera closely related to the producer (Nissen-Meyer and Nes, 1997, Archives of Microbiol., 167, p 67-77), though some can have broader inhibition spectra including food spoilage and pathogenic microorganisms (Gillor and Ghazaryan, 2007, Recent Patents on Anti-infective Drug Discovery, 2, p 115-122). Bacteriocins bind to specific receptors on target membranes to kill cells.

Bacteriocins from Gram-positive bacteria are small, ribosomally synthesized peptides produced to inhibit growth or kill other bacteria. Usually the bacteriocin producer is protected against its own bacteriocin by the immunity protein whose gene is located at the same operon as the structural gene of its corresponding bacteriocin (Diep and Nes, 2002, supra).

Dairy products are common sources for bacteriocins where species of *Lactococcus* are often prevalent as active producers. However, lactococcal bacteriocins from non-dairy sources have also been reported (Fujita et al., 2007, Applied and Environ. Microbiol., 73, p 2871-2877; Iwatani et al., 2007, Biosci Biotech. Biochem., 71, p 1984-1992). Some known lactococcal bacteriocins, namely nisin, lacticin 481, lactococcins A, B, M, G, LsbB, 972 and Q, are all produced by different *Lactococcus lactis* strains (Fujita et al., 2007, supra; Kojic et al., 2006, Canad. J. Microbiol., 52, p 1110-1120; Martinez et al., 1996, Microbiology, 142 (Pt 9), p 2393-2398; Morgan et al., 1995, Appl. Environ. Microbiol., 61, p 2995-3001; Nissen-Meyer et al., 1992, J. Bacteriol., 174, p 5686-5692; Piard et al., 1992, Appl. Environ. Microbiol., 58, p 279-284). Garvicin ML and garvicin A are also produced by *Lactococcus garvieae* strains isolated from the GIT of Mallard duck (Borrero et al., 2011, Applied and Environmental Micro., 77, p 369-373) and from a human clinical case (Maldonado-Barragan et al., 2013, Appl. Environ. Microbiol., 79, p 4336-4346), respectively. Among the aforementioned bacteriocins nisin and lacticin 481 belong to the class consisting of heavily modified peptides known as lantibiotics (Piard et al., 1992, supra) while the remaining ones belong to the non-lantibiotic class which consists of non-modified peptides or peptides with limited modifications (Cotter et al., 2005, supra). Like most bacteriocins, these lactococcal bacteriocins have relatively narrow inhibition spectra, which includes mostly lactococcal cells, except nisin that has relatively broad inhibition spectra (Borrero et al., 2011, supra).

Whilst bacteriocins produced by lactic acid bacteria (LAB) have been studied due to their generally recognized as safe (GRAS) status (Nes et al., 2007, J. Bacteriol., 189, p 1189-1198), only nisin and pediocin PA-1 have been authorized as preservatives in the food industry (Ben-mechemene et al., 2013, Recent patents on DNA and gene sequences, 7, p 66-73). Both have broad antimicrobial spectra and are produced by LAB. However, since bacteriocin activity also causes selective pressure on bacterial populations to produce resistant strains and nisin-resistant bacteria have been already reported (Kaur et al., 2014, J. Food Sci. Tech., 51, p 233-244), there remains a need for new antibacterials with broad antimicrobial spectra.

The present inventors have now surprisingly identified a new bacteriocin with a broad antibacterial spectra which is able to kill many gram-positive pathogens including problematic species of *Enterococcus, Uisteria* and *Staphylococcus* and their antibiotic-resistant derivatives. The bacteriocin is a new bacteriocin from *Lactococcus garvieae* which differs both structurally and functionally to known bacteriocins. The bacteriocin of the invention is referred to herein as Garvicin KS.

*Lactococcus garvieae* is a LAB previously known as a human opportunistic and a major fish pathogen (Russo et al., 2012, The New Microbiologica, 35, p 495-501; Vendrell et al., 2006, Comparative Immunol., Microbiol Infect. Diseases., 29, p 177-198) but at the same time *L. garvieae* is also commonly found in milk and dairy products (Mehmeti et al., 2015, Food Control., 53, p 189-194). To date four bacteriocins have been found from different *L. garvieae* isolates.

Garviecin L1-5 is a small bacteriocin with a molecular mass of about 2.5 kDa, produced by *L garvieae* L1-5 isolated from a raw cow's milk sample (Villani et al., 2001, J. Applied Microbiol., 90, p 430-439). So far garviecin L1-5 has not been characterized at the protein and genetic level, so the amino acid sequence of L1-5 is not known. Circular bacteriocin Gavicin ML with a molecular mass 6 kD consists of 60 aa, is produced by *L. garvieae* DCC4 and has been isolated from Mallard duck intestines (Borrero et al., 2011, Appl. Environ. Microbiol., 77, p 369-373; Sanchez et al., 2007, Int. J. Food Microbiol., 117, p 295-305). Thus far, Gavicin ML is the best studied among all *L. garvieae* bacteriocins (Gabrielsen et al., 2014, J. Bacteriol., 196, p 911-919; Gabrielsen et al., 2012, Antimicrobial Agents Chemoth., 56, p 2908-2915). Garvieacin Q consists of 50 aa (5.3 kD) and is produced by BCC 43578 strain isolated from fermented pork sausage (Tosukhowong et al., 2012, Appl. Environ. Microbiol., 78, p 1619-1623). Garvicin A is a 43 aa bacteriocin produced by *L. garvieae* 21881 (human clinical isolate) with a molecular weight of 4.7 kD (Maldonado-Barragan et al., 2013, Appl. Environ. Microbiol., 79, p 4336-4346).

Garvicins A and Q belong to the subclass IId which consists of linear and non-pediocin-like bacteriocins, and both bacteriocins display relatively narrow inhibition spectra containing mostly strains of *L. garvieae* and closely related species (Maldonado-Barragan et al., 2013, supra; Tosukhowong et al., 2012, supra). The inhibition spectrum of L1-5 consists of mostly closely related species and some strains of *Listeria* and *Clostridium* but not *Pediococcus* (Villani et al., 2001, supra). Garvicin ML has an apparently wider inhibition spectrum than the aforementioned ones (Borrero et al., 2011, supra), but is considerably narrower compared to that of garvicin KS.

In contrast to known bacteriocins from LAB in general and *Lactococcus garvieae* in particular, the bacteriocin of the invention is a potent bacteriocin with a broad inhibition spectrum against many important problematic bacteria of genera *Listeria*, *Staphylococcus*, *Streptococcus* and *Enterococcus*. The breath of inhibition is comparable to (and in some cases better than) that of nisin which has been approved by FAO/WHO for use as a food preservative in many countries (Paul Ross, 2002, Int. J. Food Microbiol., 79, p 3-16). Like nisin, garvicin KS is capable of killing antibiotic-resistant bacteria of *L. monocytogenes*, MRSA and VRE which are common problematic bacteria in dairy environments and/or hospital environments. As such, garvicin KS may be used as a preservative or an antimicrobial in applications dealing with pathogens and food spoilage bacteria.

The bacteriocin garvicin KS was found to have three leaderless peptides with strong sequence homology. Based on the peptide sequences a family of sequence-related bacteriocins consisting of 2-4 peptides have been identified with similarly advantageous antibacterial properties. In particular, three related bacteriocins were identified from *B. cereus* and found to have antimicrobial activity, these have been named CereinH, CereinV and CereinX. CereinH consists of four peptides, though it can also be active when only three peptides are combined. The others are three peptide bacteriocins. Other known *B. cereus* bacteriocins are single peptides.

Since some of the peptides from the different bacteriocins are very similar in sequence, peptide substitutions were carried out and novel bacteriocins with high potency were generated. Although not wishing to be limited by theory it is believed likely that this family of bacteriocins bind to the same receptor on bacterial cells.

A bacteriocin from *Staphylococcus* is known (Aureocin A70) which has four peptides. Aureocin A70 is a leaderless, plasmid-encoded, non-processed four-peptide (from 30 to 31 aa each) class II bacteriocin produced by *Staphylococcus*

*aureus* A70 (Netz et al., 2001, J. Mol. Biol., 311, p 939-949). Aureocin A70 is produced by *S. aureus* involved in bovine mastitis and quite common among *S. aureus* in Brazil and Argentina (Ceotto et al., 2012, Letts Appl. Microbiol., 54, p 455-461; Ceotto et al., 2009, Res. Microbiol., 160, p 592-599). None of the four peptides of A70 had antimicrobial activity and a synergistic effect was observed only when all four peptides were mixed together (Netz et al., 2001, supra). The family of bacteriocins of the invention have considerably better potency and breadth of spectrum antibacterial activity than A70.

The bacteriocins of the invention have considerable advantages. Unlike antibiotics bacteriocins they are active at much lower concentrations (nano- to picomolar) and they are biodegradable by proteolytic enzymes but quite unaffected by abuses such as exposure to heat, pH, organic solvents etc. (Nigam et al., 2014, Microbiol. Res., 169, p 643-651). Unlike traditional antibiotics which kill target cells by inhibiting important cellular processes, bacteriocins kill target cells by disrupting the integrity of target membranes and are very potent, being active at nM concentrations. Furthermore, due to their different mode of action, bacteriocins are active against both antibiotic sensitive bacteria as well as their antibiotic resistant counterparts. They are also particularly attractive as they are natural antimicrobials produced by LAB which are GRAS organisms.

Thus, in a first aspect the present invention provides a multi-peptide composition comprising at least:

a) a peptide comprising the sequence as set forth in SEQ ID NO:1 (GarA) or a sequence with at least 30%, preferably 50% sequence identity thereto;

b) a peptide comprising the sequence as set forth in SEQ ID NO:2 (GarB) or a sequence with at least 30%, preferably 50% sequence identity thereto; and c) a peptide comprising the sequence as set forth in SEQ ID NO:3 (GarC) or a sequence with at least 30%, preferably 50% sequence identity thereto; wherein the sequence as set forth in SEQ ID NO:1 or said sequence with at least 30%, preferably 50% sequence identity thereto comprises at least two tryptophan residues, wherein said composition has antibacterial activity.

The table below provides details of the sequences disclosed in the application.

| Name | Sequence | SEQ ID NO: |
|---|---|---|
| GarvicinKosA (GarA) | MGAIIKAGAKIVGKGVLGGGASWLGWNVGEKIWK | 1 |
| GarvicinKosB (GarB) | MGAIIKAGAKIIGKGLLGGAAGGATYGGLKKIFG | 2 |
| GarvicinKosC (GarC) | MGAIIKAGAKIVGKGALTGGGVWLAEKLFGGK | 3 |
| CereinHA (CerH-A) | MAKIGKWVVKGAAGYLGWEIGEGIWK | 4 |
| CereinHB (CerH-B) | MGALVKGGLKLIGGTAASWLGWEAGERVWK | 5 |
| CereinHC (CerH-C) | MGAIIKGGLKLVGGGAAGGFTYGGLKKIFG | 6 |
| CereinHD (CerH-D) | MGAIIKGAAKVLGKGAATGGVIYGLEKLFR | 7 |
| CereinVC (CerV-C) | MGAVVKGGLKIIGGTAASWLGWEAGTRIWK | 8 |

-continued

| Name | Sequence | SEQ ID NO: |
|---|---|---|
| CereinVB (CerV-B) | MGAAVKMLGKAFAGGVAGGATYGGLKKIFG | 9 |
| CereinVA (CerV-A) | MGAVVKGALKIIGGGAASGGAVYGLERIFGR | 10 |
| CereinX A (CerX A) | MGKKIGKWIITGAAGWAGWEIGEGIWK | 11 |
| CereinX C (CerX C) | MGALFKAALKAAGGGAAGGATYGGLKHFFG | 12 |
| CereinX B (CerX B) | MKYLGTLIKGAAGGAGAYVGEKIYNWYKN | 13 |
| GarA encoding sequence | ATGGGTGCAATTATCAAAGCAGGTGCTAAAATCGTTGGAAAAGGCGTA TTAGGAGGCGGAGCTTCTTGGCTTGGATGGAACGTCGGCGAAAAAATT TGGAAATAA | 14 |
| GarB encoding sequence | ATGGGTGCAATTATTAAAGCAGGTGCTAAAATCATTGGAAAAGGCTTA TTAGGGGGCGCAGCTGGAGGCGCTACTTATGGTGGCTTAAAAAAAATA TTTGGTTAA | 15 |
| GarC encoding sequence | ATGGGTGCAATTATCAAAGCAGGTGCTAAAATCGTTGGAAAAGGTGCA CTAACTGGTGGTGGAGTTTGGCTTGCAGAAAAATTATTTGGAGGTAAA TAA | 16 |
| Immunity protein (IP) Garvicin KS | See description | 17 |
| IP Cerein H | See description | 18 |
| IP Cerein X | See description | 19 |
| ABC transporter (ABCT) Garvicin KS | See description | 20 |
| ABCT Cerein H | See description | 21 |
| ABCT Cerein V | See description | 22 |
| ABCT Cerein X | See description | 23 |
| Primer | 5'-GGTTACCTTGTTACGACTT-3' | 24 |
| Primer | 5'-TAACACATGCAAGTCGAACG-3' | 25 |
| Primer | 5'-GTGGTGGTGGTGGTG-3' | 26 |
| pspC receptor (Lactococcus lactis) | MSQRQLTKSVTNRRVSGVIAGIAEYFGLGRDVVTILRILFVVLAFGSW GGLIPLYFVASWIIPSARPRNYYDDSEDDYQEKWNRKAQHFDEKMDRW SERYSDKMNNWARRYEDKGRQNQQDSNQWGNPWDEPKSRKTKEAQPVE KEKEDDWSD | 27 |
| A70A | MGKLAIKAGKIIGGGIASALGWAAGEKAVGK | 28 |
| A70B | MGAVAKFLGKAALGGAAGGATYAGLKKIFG | 29 |
| A70O | MGALIKTGAKIIGSGAAGGLGTYIGHKILGK | 30 |
| A70D | MGAVIKVGAKVIGWGAASGAGLYGLEKILKK | 31 |
| GarA-23A | MGAIIKAGAKIVGKGVLGGGASALGWNVGEKIWK | 32 |
| GarA-26A | MGAIIKAGAKIVGKGVLGGGASWLGANVGEKIWK | 33 |
| GarA-33A | MGAIIKAGAKIVGKGVLGGGASWLGWNVGEKIAK | 34 |

As referred to herein a "multi-peptide composition" refers to a composition comprising at least the three recited peptides (e.g. only three peptides). Further peptides may also be present, thus the composition may additionally comprise one or more further peptides (e.g. 4 or 5 peptides in total).

Although not wishing to be bound by theory it is believed that the peptides associate with one another and may form a temporary or permanent complex to achieve their functionality. In a preferred feature the peptides exhibit synergy when used together as antibacterial in methods and uses described herein. As used herein "complex" refers to discrete molecules which are associated with one another through binding interactions (i.e. act as binding partners to one another) but generally do not form covalent bonds. Such molecules are "associated" with one another when they form specific interactions such that they are in contact with one another. However, the invention extends to compositions in which the peptides form into a complex as well as compositions in which the peptides do not form a complex.

As preferred to herein a "peptide" is a polymer comprising at least 15 amino acids, preferably at least 25 or 30 amino acids. Preferably the peptides contain less than 50, e.g. less than 40 or 35 amino acids. In a preferred aspect, each of the peptides in said composition is from 25 to 40 amino acids in length, preferably from 30 to 35 amino acids in length. Preferably each peptide is cationic.

The amino acids making up the peptide may be natural L or D amino acids (preferably L amino acids). Alternatively, one or more non-naturally occurring amino acids may be present in the peptides. Such non-naturally occurring amino acids are derivatives of naturally occurring amino acids and include alkyl (e.g. methyl), nor and aminoalkyl derivatives. Appropriate derivatives are selected to maintain functionality.

The peptides of the invention also include those which are modified without affecting the sequence of the peptide, e.g. by chemical modification, including by deglycosylation or glycosylation. Such peptides may be prepared by post-synthesis/isolation modification of the peptide without affecting functionality, e.g. certain glycosylation, methylation etc. of particular residues. The peptides of the invention may also take the form of peptidomimetics which may be considered derivatives in which the functional features of the peptide are retained but are presented in the context of a different, e.g. non-peptide structure. Such peptidomimetics have successfully been developed and used in the art, particularly for medical applications. Peptidomimetics, particularly non-peptidic molecules may be generated through various processes, including conformational-based drug design, screening, focused library design and classical medicinal chemistry. Not only may oligomers of unnatural amino acids or other organic building blocks be used, but also carbohydrates, heterocyclic or macrocyclic compounds or any organic molecule that comprises structural elements and conformation that provides a molecular electrostatic surface that mimics the same properties of the 3-dimensional conformation of the peptide may be used and prepared by methods known in the art.

Thus the peptidomimetics may bear little or no resemblance to a peptide backbone. Peptidomimetics may comprise an entirely synthetic non-peptide form (e.g. based on a carbohydrate backbone with appropriate substituents) or may retain one or more elements of the peptide on which it is based, e.g. by derivatizing one or more amino acids or replacing one or more amino acids with alternative non-peptide components. Peptide-like templates include pseudo-peptides and cyclic peptides. Structural elements considered redundant for the function of the peptide may be minimized to retain a scaffold function only or removed where appropriate.

When peptidomimetics retain one or more peptide elements, i.e. more than one amino acid, such amino acids may be replaced with a non-standard or structural analogue thereof. Amino acids retained in the sequences may also be derivatised or modified (e.g. labelled, glycosylated or methylated) as long as the functional properties of the peptides of the invention, or for use according to the invention, are retained. The peptidomimetics are referred to as being "derivable from" a certain peptide sequence. By this it is meant that the peptidomimetic is designed with reference to a defined peptide sequence, such that it retains the structural features of the peptide which are essential for its function. This may be the particular side chains of the peptide, or hydrogen bonding potential of the structure. Such features may be provided by non-peptide components or one or more of the amino acid residues or the bonds linking said amino acid residues of the peptide may be modified so as to improve certain functions of the peptide such as stability or protease resistance, while retaining the structural features of the peptide which are essential for its function.

Examples of non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids and D-N-methylamino acids.

The peptides also include derivatives which have been modified, e.g. to facilitate their use in pharmaceutical applications (discussed below), e.g. by the addition of targeting or functional groups, e.g. to improve lipophilicity, aid cellular transport, solubility and/or stability. Thus oligosaccharides, fatty acids, fatty alcohols, amino acids, peptides or polypeptides may be conjugated to the aforementioned peptides.

The peptides also encompass derivatives in the form of "pro-drugs" or "pro-peptides" such that the added component may be removed by cleavage once administered, e.g. by cleavage of a substituent added through esterification which may be removed by the action of esterases. Such pro-drugs include native precursors of the naturally occurring peptides which are cleaved e.g. by proteolysis to yield the peptide of interest. Such precursors may be inactive in the precursor form but may be activated by proteolytic cleavage.

Preferably the peptide sequences defined herein are at least 35, 40, 45, 55, 60, 65, 70, 75, 80, 85, 90, 95, 96, 97, 98 or 99% identical to the sequence (SEQ ID NOs 1-3, and other peptide sequences described hereinafter) to which the peptide sequence is compared. In a preferred feature said sequence identity in any one of a), b) and/or c) is at least 60, 70, 80, 90 or 95% sequence identity.

Sequence identity may be determined by, e.g. using the SWISS-PROT protein sequence databank using FASTA pep-cmp with a variable pamfactor, and gap creation penalty set at 12.0 and gap extension penalty set at 4.0, and a window of 2 amino acids. Preferably said comparison is made over the full length of the sequence, but may be made over a smaller window of comparison, e.g. less than 50, 40, 30 or 20 contiguous amino acids.

Hereinafter reference is also made to sequence identity in relation to nucleic acid sequences. Preferably the defined nucleic acid sequences may have at least 91, 92, 93, 94, 95, 96, 97, 98, 99 or 100% sequence identity to the sequence to which is it compared. Sequence identity may be determined by, e.g. FASTA Search using GCG packages, with default values and a variable pamfactor, and gap creation penalty set at 12.0 and gap extension penalty set at 4.0 with a window of 6 nucleotides. Preferably said comparison is made over the full length of the sequence, but may be made over a smaller window of comparison, e.g. less than 150, 120, 90 or 60 contiguous nucleotides.

In a preferred aspect the sequence as provided in the SEQ ID NO:1 to 3 (and other peptide sequences described herein) provides the peptide to be used (i.e. has 100% sequence identity). The peptide may consist of this sequence or comprise this sequence in a longer peptide, i.e. may contain flanking sequences, e.g. of 1-10 amino acids at the N and/or C-terminal end. These flanking sequences may be ignored in calculating sequence identity. The sequences provided in the SEQ ID NOs given for the peptides may also be truncated, e.g. up to 5 amino acids from the N and/or C terminal may be removed (e.g. 1, 2, 3, 4 or 5, e.g. 1-3 amino acids at one or both terminals and/or 1-10, e.g. 1, 2, 3, 4 or 5 amino acids in total). Preferably the N-terminal amino acids are truncated. In determining the sequence identity between truncated peptides and the sequences set out in the SEQ ID NOs, the comparison window should include the truncated sequences, i.e. a truncated peptide in which 2 amino acids are removed from each end of the sequence is calculated to have a 4 amino acid mismatch and the sequence identity calculated accordingly.

Deletions, insertions and substitutions of the disclosed peptide sequences are also contemplated. In a preferred aspect, the peptide sequences in compositions of the invention may comprise at least one, two or three deletions, insertions or substitutions relative to the sequences presented in the SEQ ID NO.

Preferably such sequence identity related peptides, and peptides containing non-natural amino acids are functionally equivalent to the peptides which are set forth in the recited SEQ ID NOs. Peptides which show "functional equivalence" exhibit the same or substantially the same antibacterial effects as the peptide from which they are derived (by sequence variation or use of different amino acids). The antibacterial effects may be assessed by providing the peptide in a composition with the other peptides which make up the bacteriocin (e.g. peptides with SEQ ID NOs 2 and 3 in the case of a peptide derived from SEQ ID NO:1) and testing its antibacterial effects against a panel of bacteria. Preferably a functionally equivalent peptide when tested as a composition has at least 90% of the antibacterial activity exhibited by Garvicin KS on a strain of bacteria selected from the genera *Enterococcus, Listeria* and *Staphylococcus*. Preferably the strain is a strain as set forth in Table 3 (e.g. *E. faecium* LMGT 2772) or the commonly used laboratory strain *L. lactis* IL1403. Antibacterial activity may be determined by reference to the MIC value, minimum inhibition concentration (MIC), which is defined as the minimum amount of bacteriocin that inhibits at least 50% of the growth of the bacteria in 200 µL of culture.

Particularly preferred functionally-equivalent variants are natural biological variations (e.g. allelic variants or geographical variations). In an alternative embodiment the variants may be non-natural, or may be provided in a composition in which the different peptides are not provided together in nature.

Peptide a) as set forth above (comprising SEQ ID NO:1, GarA) or a sequence-related peptide comprises at least two tryptophan residues (or non-natural derivatized amino acids of tryptophan). These tryptophans may appear anywhere in the peptide sequence, but preferably appear in the C-terminal end of the peptide, e.g. in the 15 residues at the C-terminal end. Conveniently more than 2 tryptophans may be present, e.g. 3 or 4 tryptophans.

As described in the Examples, tryptophans have been found to be important for the activity of the bacteriocins of the invention, in particular the tryptophan at position 26 in GarA (SEQ ID NO:1) of Garvicin KS. Thus, in a preferred aspect, at least one peptide, e.g. peptide a) comprises a consensus sequence $X^1Y^1GWY^2Y^3GY^4Y^5YX^2K$, wherein $X^1$, $X^2$ and each Y may be any amino acid. Preferably this consensus sequence appears at the C-terminus of the peptide in which it appears. In a particularly preferred aspect, $X^1$ and $X^2$ may each be any amino acid, with the proviso that at least one of $X^1$ and $X^2$ is a tryptophan residue. Thus the consensus sequence may be $WY^1GWY^2Y^3GY^4Y^5Y^6X^2K$, $X^1Y^1GWY^2Y^3GY^4Y^5Y^6WK$
or
$WY^1GWY^2Y^3GY^4Y^5Y^6WK$.

Particularly preferably the consensus sequence satisfies one or more of the following:

a) $X^1$ and $X^2$ are both tryptophan residues;
b) $Y^1$ is an alanine or leucine residue;
c) $Y^2$ is a glutamic acid residue;
d) $Y^3$ is a hydrophobic amino acid residue selected from alanine, valine, leucine, isoleucine, proline, or methionine, preferably alanine, valine or isoleucine;
e) $Y^4$ is a glutamic acid residue; and
f) $Y^6$ is an isoleucine residue.

In a further preferred aspect the consensus sequence may have the form: $Z^1Z^2Z^3X^1Y^1GWY^2Y^3GY^4Y^5YX^2K$, wherein $X^1$, $X^2$ and each Y and each Z may be any amino acid. Preferably $X^1$, $X^2$ and each Y are as indicated above. In a preferred aspect $Z^1$ and/or $Z^2$ may be an alanine residue, and/or $Z^3$ may be a serine or glycine residue.

Thus, for example, the consensus sequence may have the form:

$Z^1AZ^3X^1Y^1GWY^2Y^3GY^4Y^5Y^6WK$;

$Z^1AZ^3X^1Y^1GWY^2Y^3GY^4Y^5IWK$;

$AAZ^3WY^1GWEY^3GEY^5IWK$.

Compositions of the invention have antibacterial activity. As used herein "antibacterial activity" refers to the ability of the compositions to kill, damage or prevent the replication of selected bacteria under in vitro conditions, e.g. as set forth in the Examples. Damage refers to affecting the bacteria's ability to function normally, such that it may die or be unable to replicate. Preferably a treatment, use or method described herein results in the death or damage of at least 25, 50, 75 or 90% of the bacteria to which the treatment is applied or prevents replication such that a bacterial infection is prevented or reduced, e.g. by at least 30, 40, 50, 60, 70, 80 or 90% relative to a control to which the treatment is not applied. In particular, the antibacterial activity is assessed by determining the MIC value against one or more bacteria. The bacteria to be tested may be selected from a strain of bacteria selected from the genera *Enterococcus, Listeria* and *Staphylococcus*. Preferably the strain is a strain as set forth in Table 3 (e.g. *E. faecium* LMGT 2772) or *L. lactis* IL1403. A composition with antibacterial activity has a MIC value of less than 300 nM, preferably less than 50 nM, especially preferably less than 15 nM, preferably against *L. lactis* IL1403.

The bacteriocins of the invention comprise family members Cerein C, Cerein X and Cerein H and these bacteriocins and related sequences form further preferred aspects of the invention. The peptides making up these bacteriocins are related to the peptides making up Garvicin KS as follows:

| Garvicin KS peptide | Related Cerein peptide |
|---|---|
| A: GarvicinKosA (GarA) (SEQ ID NO: 1) | CereinHA (CerH-A) (SEQ ID NO: 4), CereinHB (CerH-B) (SEQ ID NO: 5); CereinVC (CerV-C) (SEQ ID NO: 8); CereinX A (CerX A) (SEQ ID NO: 11) |
| B: GarvicinKosB (GarB) (SEQ ID NO: 2) | CereinHC (CerH-C) (SEQ ID NO: 6); CereinVB (CerV-B) (SEQ ID NO: 9); CereinX C (CerX C) (SEQ ID NO: 12) |
| C: GarvicinKosC (GarC) (SEQ ID NO: 3) | CereinHD (CerH-D) (SEQ ID NO: 7); CereinVA (CerV-A) (SEQ ID NO: 10); CereinX B (CerX B) (SEQ ID NO: 13) |

Thus, in a preferred aspect, bacteriocins of the invention comprise (or consist of) one or more peptides (or sequences with at least 30%, preferably 50% sequence identity thereto or an alternative sequence identity as described hereinbefore) from each of the above groups A to C. Preferably the bacteriocins of the invention contain at least one peptide containing the consensus sequence described hereinbefore.

Preferred combinations are set out below. In one aspect, preferably the peptides have the indicated sequence or in an alternative embodiment the peptides and/or the combination of peptides in the composition is non-native, i.e. does not occur in nature. The above definitions and descriptions relating to peptides of the invention apply equally to the peptides and compositions described hereinbelow.

Thus the present invention provides a composition as defined hereinbefore wherein said composition comprises:
a) a peptide comprising the sequence as set forth in SEQ ID NO:1 (GarA) or a sequence with at least 80% sequence identity thereto; b) a peptide comprising the sequence as set forth in SEQ ID NO:2 (GarB) or a sequence with at least 80% sequence identity thereto; and
c) a peptide comprising the sequence as set forth in SEQ ID NO:3 (GarC) or a sequence with at least 80% sequence identity thereto;
wherein the sequence as set forth in SEQ ID NO:1 or said sequence with at least 80% sequence identity thereto comprises at least two tryptophan residues. These may be considered the Garvicin KS family of bacteriocins. The at least two tryptophans are preferably in the consensus sequence described hereinbefore.

In a further preferred aspect, the present invention provides a composition, preferably as defined hereinbefore, wherein said composition comprises:
a) a peptide comprising the sequence as set forth in SEQ ID NO:4 (CerH-A) or a sequence with at least 80% sequence identity thereto and/or a peptide comprising the sequence as set forth in SEQ ID NO:5 (CerH-B) or a sequence with at least 80% sequence identity thereto;
b) a peptide comprising the sequence as set forth in SEQ ID NO:6 (CerH-C) or a sequence with at least 80% sequence identity thereto; and
c) a peptide comprising the sequence as set forth in SEQ ID NO:7 (CerH-D) or a sequence with at least 80% sequence identity thereto;
wherein the sequence as set forth in SEQ ID NO:4 or said sequence with at least 80% sequence identity thereto and/or the sequence as set forth in SEQ ID NO:5 or said sequence with at least 80% sequence identity thereto comprises at least two tryptophan residues and said composition has antibacterial activity. These may be considered the Cerein H family of bacteriocins. The at least two tryptophans are preferably in the consensus sequence described hereinbefore.

In a further preferred aspect, the present invention provides a composition, preferably as defined hereinbefore, wherein said composition comprises:
a) a peptide comprising the sequence as set forth in SEQ ID NO:8 (Cerv-C) or a sequence with at least 80% sequence identity thereto;
b) a peptide comprising the sequence as set forth in SEQ ID NO:9 (Cerv-B) or a sequence with at least 80% sequence identity thereto; and
c) a peptide comprising the sequence as set forth in SEQ ID NO:10 (Cerv-A) or a sequence with at least 80% sequence identity thereto;
wherein the sequence as set forth in SEQ ID NO:8 or said sequence with at least 80% sequence identity thereto comprises at least two tryptophan residues and said composition has antibacterial activity. These may be considered the Cerein V family of bacteriocins. The at least two tryptophans are preferably in the consensus sequence described hereinbefore.

In a further preferred aspect, the present invention provides a composition, preferably as defined hereinbefore, wherein said composition comprises:
a) a peptide comprising the sequence as set forth in SEQ ID NO: 11 (CerX A) or a sequence with at least 80% sequence identity thereto;
b) a peptide comprising the sequence as set forth in SEQ ID NO:12 (CerX C) or a sequence with at least 80% sequence identity thereto; and
c) a peptide comprising the sequence as set forth in SEQ ID NO:13 (CerX B) or a sequence with at least 80% sequence identity thereto;
wherein the sequence as set forth in SEQ ID NO:11 or said sequence with at least 80% sequence identity thereto comprises at least two tryptophan residues and said composition has antibacterial activity. These may be considered the Cerein X family of bacteriocins. The at least two tryptophans are preferably in the consensus sequence described hereinbefore.

The above and below definitions of sequence identity may also have the values as described hereinbefore.

As discussed above, and as illustrated in the Examples, peptides from the different bacteriocin sub-families may be substituted for one another but still retain advantageous, potent, antibacterial activity. Thus in a further preferred aspect the present invention provides a composition, preferably as described hereinbefore, wherein said composition comprises:
a) one or more peptide comprising a sequence as set forth in any one of SEQ ID NOs:1, 4, 5, 8 or 11 (A) or a sequence with at least 80% sequence identity thereto;
b) a peptide comprising a sequence as set forth in SEQ ID NO:2, 6, 9 or 12 (B) or a sequence with at least 80% sequence identity thereto; and
c) a peptide comprising a sequence as set forth in SEQ ID NO:3, 7, 10 or 13 (C) or a sequence with at least 80% sequence identity thereto;
wherein the sequence as set forth in SEQ ID NO:1, 4, 5, 8 or 11 or said sequence with at least 80% sequence identity thereto comprises at least two tryptophan residues and said composition has antibacterial activity.

When one or more of the a) peptides are present, preferably two or three of such peptides are present. For example, peptides comprising SEQ ID NOs: 4 and 5 (or related sequences as defined) may be provided in the composition. Preferred combinations are as set forth in the examples (as well as related sequences thereto, as defined herein).

The peptides described herein may be prepared by any convenient means known in the art, e.g. direct chemical synthesis or by recombinant means by expressing a nucleic acid molecule of the appropriate encoding sequence in a cell. Thus the peptides provided may be synthetic or recombinant, i.e not produced in the bacteria in which they were identified. Alternatively the peptides/compositions may be produced from host cells as described hereinafter (e.g. from the deposited host cell). The peptides/composition of the invention may be isolated or purified after production.

The composition described herein may also comprise impurities, e.g. after the preparation of said composition from one of the natural sources described herein or after synthesis of the peptides. In compositions as described herein, the peptides may be present (in combination) in the range 0.001 to 10% w/w of the composition. Thus each peptides may be present in the range of $2.5 \times 10^{-4}$ to 2.5% w/w of the composition. The composition may be treated to enrich the peptides (e.g. after chemical synthesis or production in host cells) or may be used without further purification, e.g. the supernatant of the host cell expressing the peptides which form the composition. Host cells expressing the peptides of the invention are described in more detail hereinafter.

As referred to herein, "purification" refers to removing contaminants from a sample. The peptides or nucleic acid molecules described herein are preferably substantially free of any contaminating components derived from the source material or materials used in the isolation procedure or in their synthetic preparation. Especially preferably the peptide(s) or nucleic acid molecule(s) is purified to a degree of purity of more than 50 or 60%, e.g. >70, 80 or 90%, preferably more than 95 or 99% purity as assessed w/w (dry weight). Such purity levels correspond to the specific molecule of interest, but includes its degradation products. Where appropriate, enriched preparations may be used which have lower purity, e.g. contain more than 1, 2, 5 or 10% of the molecule of interest, e.g. more than 20 or 30%. The peptides of the invention may be purified by, for example, chromatography (e.g. HPLC, size-exclusion, ion-exchange, affinity, hydrophobic interaction, reverse-phase) or capillary electrophoresis.

Preferably the peptides that are present are provided in the ratio 0.5-2:0.5-2:0.5-2 when three peptides are present and 0.5-2:0.5-2:0.5-2:0.5-2 when four peptides are present, wherein preferably said peptides are provided in equimolar amounts in the composition.

Whilst in a preferred aspect the native sequences of Garvicin KS, Cerein H, X and V peptides are used, in another aspect, non-native sequences and/or combinations may be used. Thus, in a preferred aspect a composition as described herein is not:
i) a composition with three peptides with the sequences as set forth in SEQ ID NOs:1, 2 and 3;
ii) a composition with four peptides with the sequences as set forth in SEQ ID NOs:4, 5, 6 and 7;
iii) a composition with three peptides with the sequences as set forth in SEQ ID NOs:8, 9 and 10; or
iv) a composition with three peptides with the sequences as set forth in SEQ ID NOs:11, 12 and 13.

The composition has antibacterial activity against a broad spectrum of bacteria. Preferably the composition has antibacterial activity against at least one bacteria selected from the genera *Bacillus, Streptococcus, Listeria, Enterococcus, Staphylococcus, Acinetobacter* and *Paenibacillus*. Especially preferably the composition has antibacterial activity against at least one bacteria selected from the species *Bacillus cereus, Listeria monocytogenes, Listeria innocua, Listeria grayi, Listeria seelingeri, Streptococcus thermophylus, Streptococcus agalactia, Streptococcus pneumonia, Streptococcus salivarius, Enterococcus faecalis, Enterococcus faecium, Staphylococcus aureus, Acinetobacter baumanii, Acinetobacter nosocomialis* and *Paenibacillus larvae*, particularly preferably Methicillin-resistant *Staphylococcus aureus* (MRSA), antimicrobial resistant (AMR) *Acinetobacter baumanii*, Vancomycin-resistant *Entercocci* (VRE) and antibiotic-resistant strains of *Listeria monocytogenes*. Preferably said composition has antibacterial activity against at least one bacteria from each of the genera *Bacillus, Streptococcus, Listeria, Enterococcus, Staphylococcus, Acinetobacter* and *Paenibacillus*. Preferred strains against which the compositions have activity are provided in the Examples.

The compositions described herein may further comprise an additional antibacterial agent. Antibacterial agents in this context refer to agents which are able to kill one or more bacteria though not necessarily with the same potency as the bacteriocins of the invention. Appropriate agents include additional bacteriocins or antibiotics. Preferred antibiotics include penicillins (such as penicillin and amoxicillin), cephalosporins (such as cephalexin (Keflex)), macrolides (such as erythromycin (E-Mycin), clarithromycin (Biaxin) and azithromycin (Zithromax)), fluoroquinolones (such as ofloxacin (Cipro), levofloxacin (Levaquin) and ofloxacin (Floxin)), sulfonamides (such as co-trimoxazole (Bactrim) and trimethoprim (Proloprim)), tetracyclines (such as tetracycline (Sumycin, Panmycin) and doxycycline (Vibramycin)) and aminoglycosides (such as gentamicin (Garamycin) and tobramycin (Tobrex)). Preferred bacteriocins include nisin and pediocin PA-1. In addition more than one (e.g. two or three) of the bacteriocins of the invention may be used in the composition, e.g. a co-mixture of Garvicin KS and one or more of Cerein X, V or C (or their related sequences defined herein).

In a further aspect the present invention provides nucleic acid molecules which encode the peptides of Garvicin KS and their related sequences (as defined herein). Thus, the present invention provides a nucleic acid molecule comprising:
i) a nucleotide sequence encoding at least one of
 a) a peptide comprising the sequence as set forth in SEQ ID NO:1 (GarA) or a sequence with at least 90% sequence identity thereto;
 b) a peptide comprising the sequence as set forth in SEQ ID NO:2 (GarB) or a sequence with at least 90% sequence identity thereto; and
 c) a peptide comprising the sequence as set forth in SEQ ID NO:3 (GarC) or a sequence with at least 90% sequence identity thereto;
wherein the sequence as set forth in SEQ ID NO:1 or said sequence with at least 90% sequence identity thereto comprises at least two tryptophan residues, wherein preferably a) is a peptide comprising or consisting of the sequence as set forth in SEQ ID NO:1 (GarA), b) is a peptide comprising or consisting of the sequence as set forth in SEQ ID NO:2 (GarB), and/or c) is a peptide comprising or consisting of the sequence as set forth in SEQ ID NO:3 (GarC); or
ii) a nucleotide sequence comprising at least one of
 a) a nucleotide sequence as set forth in SEQ ID NO:14 (GarA) or a sequence with at least 90% sequence identity thereto;
 b) a nucleotide sequence as set forth in SEQ ID NO:15 (GarB) or a sequence with at least 90% sequence identity thereto; and c) a nucleotide sequence as set forth in SEQ ID NO:16 (GarC) or a sequence with at least 90% sequence identity thereto;

wherein the sequence encoded by the sequence as set forth in SEQ ID NO:14 or said sequence with at least 90% sequence identity thereto comprises at least two tryptophan residues, wherein preferably a) is a nucleotide sequence comprising or consisting of the sequence as set forth in SEQ ID NO:14 (GarA), b) is a nucleotide sequence comprising or consisting of the sequence as set forth in SEQ ID NO:15 (GarB), and/or c) is a nucleotide sequence comprising or consisting of the sequence as set forth in SEQ ID NO:16 (GarC). Preferably the nucleic acid molecule encodes a peptide as described hereinbefore, e.g having a consensus sequence as described hereinbefore.

Preferred sequence identity values are described hereinbefore. Preferably such sequence identity related sequences are functionally equivalent to the nucleic acid molecules which are set forth in the recited SEQ ID NOs. Such functionally equivalent nucleic acid molecules preferably encode peptides which would be considered functional equivalents as described hereinbefore.

As defined herein a nucleic acid molecule may be single or double stranded DNA, cDNA or RNA, preferably DNA. Ideally however the molecules are DNA or cDNA. Functionally equivalent molecules may also be provided, e.g. in which non-native bases are used.

Whilst native molecules may be used, in one embodiment non-native nucleic acid molecules are provided, e.g. which contain at least one, two or three nucleotide modifications (e.g. addition, deletion or substitution) relative to the native sequence.

The polynucleotides described herein may be provided as free molecules (e.g. providing just the encoding or RNA sequence), or may be provided in a recombinant construct, e.g. operatively linked with regulatory, control, marker or other sequences of interest, to allow intracellular expression of the peptides of the invention, or for use according to the invention, as a gene product, the expression of which is directed by the gene(s) introduced into cells of interest.

In a preferred aspect, all of the above sequences encoding the peptides may be provided on a single nucleic acid molecule. Expression in this case allows equimolar amounts of the peptides to be produced. Conveniently they may be provided on a recombinant nucleic acid molecule. Thus the present invention provides a recombinant nucleic acid molecule comprising:

a) a regulatory sequence, and b) at least one nucleotide sequence as defined hereinbefore (Garvicin KS or related sequences) and/or nucleotide sequences encoding each of the peptides present in the composition as defined hereinbefore (e.g. Cerein peptides or related sequences). In the latter case, the recombinant nucleic acid molecule comprises a regulatory sequence and all of the nucleotide sequences which encode the peptide of a composition of the invention.

A "recombinant nucleic acid molecule" as referred to herein is a non-native nucleic acid molecule. The molecule contains a regulatory sequence which is not a regulatory sequence found in conjunction with the encoding sequences to which it is attached, i.e. the encoding sequences are heterologous relative to the regulatory sequence. Where appropriate the recombinant nucleic acid molecule may be in the form of an expression cassette to allow expression. Appropriate expression vectors include appropriate control sequences such as for example translational (e.g. start and stop codons, ribosomal binding sites) and transcriptional control elements (e.g. promoter-operator regions, termination stop sequences) linked in matching reading frame with the nucleic acid molecules as described herein. Appropriate promoters may be used to allow low, high or inducible expression. Appropriate vectors may include plasmids and viruses (including both bacteriophage and eukaryotic viruses). Thus, the nucleic acid molecules, e.g. in the form of recombinant constructs, may be presented in a vector molecule, e.g. in a plasmid. Suitable viral vectors include baculovirus and also adenovirus, adeno-associated virus, herpes and vaccinia/pox viruses. Many other viral vectors are described in the art. Preferred vectors include bacterial and mammalian expression vectors pGEX-KG, pEF-neo and pEF-HA. One or more constructs, vector molecules and/or plasmids may be used for the nucleic acid molecules as described in more detail hereinafter.

To allow expression, conveniently a recombinant nucleic acid molecule, e.g. in the form of a vector or plasmid, may be used for incorporation in the genome or for independent replication or transient transfection/expression in a cell. Conveniently integration into the genome is achieved, e.g. by homologous recombinant technology. Suitable transformation or transfection techniques are well described in the literature and may be used to introduce such vectors into prokaryotic or eukaryotic cells for expression. Alternatively, the naked nucleic acid molecule (e.g. DNA molecule) may be introduced directly into the cell for the uses described herein.

In addition, to enhance expression, the sequences of the peptides may also be expressed with a relevant immunity protein and/or proteins involved in the transport of the bacteriocins (the so-called ABC-transporters). These may be selected based on the bacteriocin which is expressed. Thus if Garvicin KS is to be expressed (or a closely sequence-related bacteriocin) the immunity protein and/or structural proteins for that bacteriocin may be used. Sequences of the immunity proteins and ABC-transporters for Garvicin KS, Cerein H, V and X are provided below. Preferably these sequences are all expressed on a single nucleic acid molecule but alternatively may be expressed on separate molecules which are co-expressed in the same host cell. Thus in a preferred aspect the nucleic acid molecule of the invention and/or the recombinant construct additionally provides an immunity protein and/or an ABC-transporter as set for in any one of SEQ ID NOs: 17 to 23 or a sequence with at least 80, 90, 95 or 98% sequence identity thereto.

Immunity Proteins:

```
SEQ ID NO: 17: Garvicin KS
MLYFGGKNMKKINDERIIKKDNEIITRTFILMFVLSLFYIVLFNKVVFF

REQPQATIFSIIIITTVYFIFDSFISKTLFVNIQEKNDVLKKVSHICSL

IIAFDTLFILLSLTKKINIDLNLDTIIVLLSLNIFLFISYYAILRLWVK

WIK*

SEQ ID NO: 18: Cerein H
MEKLKNSFSLSTHSDERIQQIEMKIWAQSGIVVLLLAFIDFIIRGLYLQ

RPFLEWAATLAIICYIVFFLIRSVLAGVYETDIHNKEQLNKKLKEKMVN

TFIFCFVAISITTYRNQLPENITGWLLVILKFIIVFSLIFGIQYLIAKF

TWYKNNKN*

SEQ ID NO: 19: Cerein X
MERLKKWFSLNTHPDERIQQIEMKIWAQSGIIVLLIAFIDFIIRGAYLH
```

RPFLEWAASLAIIFYMIFFFIKSILTGIYETDINNKEQLNEKLKEKMSN

TLIFCFVAIGTTTYKYNLPEDFIGWLSVIARFIILFAFLFGIQYLITKY

TWYKNNKN*

ABC Transporters

SEQ ID NO: 20: Garvicin KS
MKRNIKNIINIVNIKKRTLFLGIIFSLLGTLASLSLPLILKNIIDSLINK

NFNIYLVIFLCSLAIFDIIFAGMSIYLLSKVGEEVVLGLRKKIWLKILNS

KSDFFEHNSQGELVSRIMDDTKKLMDIFSTDASDFVTGLFTLIGTVVILM

TIDPLLTALIFISIPIIVLIVIPLGKSLYKFSIKIQENNAIASEYIVDRV

SNIKLIKMSNTLFEELYSGIELFRNIYKINMNRNKIQSVVLPIITLTITS

TIIGIVFFGAFRVINGALSPGALFAFVVYIVQVTGPLITILTFWNKLNTA

IGSSDRIIDILNYLEEDNIENIEKDSNYSIDYLALDHINFSIDDTKIIKD

FSYIFKKGNFYNLLGYSGSGKTTIFNIICKFITPDTGSLYTNHTNNYNIY

AWRENISYVSQDISIINGTLKENILYGVKQSYSDEFLLALLQEIGLKKLL

KQLPDGLNTKISKNSSLLSGGEKQRIALLRGCLSDKQILLVDEVSSNVDS

KNDFRIYSFLKNHNDNKIIIMITHKLSNINNEDPILLLENGKLIASGLKN

EVSKSSSLFKELENYYRGNINNEYLMSQD*

SEQ ID NO: 21: Cerein H
MGKDKDVSLKALWEITTPPKVTLFWGIIFGLINSGCSLIIPLILKEQIEQ

LSKGFSYELLLLVLLLLIVEIISMSLSLYLLSLVGQRVVLNLRKMIWRKI

LNLKVDFYSKNQPGEIISRVTNDTTVTMNLLSNEIADLFSSGLSMIGAVV

ILFLLDVPMTLTLLSAIPVTLFIVIPISRKlYKVSYEQQEKMSEFTALLS

QVLGEIRLIKSYGTEDFEFERGKKKIEELYVNGMKRAKIESILIPLMTVS

ITLIIVVVVGFGSYRVSEGYLSSGELLAFILYLFQIVGPVGVMSRFITSV

QSAKGSTERIFNILDEKDEKTKVNFLEEPSFGILELKGLNFGYGEKSIFE

NINLKIMPNTVTALVGPSGVGKTTLFYLLERFYDPLKGEILLDGKSHLDI

DLDKWRAMFSYVSQDCPILAGTIRENITYGIQREVSKDEIIKASVLANCH

EFITSFSDGYNTILGERGINLSGGQKQRISIARAFLRDTPFLLLDEATAN

LDTNSENMIKHALDKLIYKKTTIVIAHRISTIQNADQIIVLDQGEISGFG

THDQLIKSNKLYQLLSNQQKMTS*

SEQ ID NO: 22: Cerein V
MLRFTERFKEYIFMKKEKTMSLRTLWKTTNPPNTPLIFGIILSLINTSCS

LVIPLILKKQIEQLDNGFSYKLLGLILFLLLIEIISMGISLYLLSLVGQK

VVLNLRTILWKKILNLKVDFYNKNQPGEVISRVTNDTTVAMNLLSTEIAD

VLSGVLSMIGSVIILFILDVPMTVTLLSAIPITLFIVIPISKKIYKVSYE

QQEKMSDFTALLSQVLSEIRLIKSYNTENYEFERGKTKIEALYKNGMKRA

KVESILIPLMTVVITTIIVVIVGFGSYRVSKGYISSGELLAFILYLFQIV

APVGTMSRFITSVQSTKGATERIFDILNKKEEKEKIASFENPSFGILDFK

NVSFGYDEKTILNNISFQVIPNTVTAIVGPSGVGKTTLFYLLERFYTPTC

GEISLNGKPQLNIELEKWRSMFSYVSQDCPILVGTIKENILYGIQRKVSE

EEIIKVSNLANCHNFITELPNGYDTKLGERGINISGGQKQRIAIARALLR

NAPFLLLDEATANLDTKSEIMIKEAMEKLIYGKTTIVIAHRISTIQNADQ

IIVLDKNGISGMGTHEQLLEKNELYQDLANQNHKAEINECVKP*

SEQ ID NO: 23: Cerein X
MEKDKDVSLKALWEITTPPKVTLFWGVIFGLINSGCSLIIPLILKEQIEQ

LSEGFSYELLFLVLFLLIVEIISMGFSLYLLSLVGQRVVLNLRKMIWRKV

LNLKVDFYSKNQPGEIISRVTNDTTVTMNLLSSEIADLLSGVLSMIGAVA

ILFLLDVPMTLTLLSAVPVTLFIVIPISKKIYKVSYAQQEKMSEFTALLS

QVLGEIRLIKSYGTEDFEFERGKKKIEELYVNGIKRAKIESILIPLMTVS

ITLIIVVVVGFGSYRVSEGYLSSGELLAFILYLFQIVGPVGVMSRFITNV

QSAKGSTERIFNILDEKDEKNKGDFLEEPSFGILEFKDIGFAYDEKNIFE

NINLKIMPNTVTALVGPSGVGKTTLFYLLERFYDPLKGEILLDGKSHLNI

DLDKWRSMFSYVSQDCPILVGTIRENIIYGIQREVSEDEIIKASILANCH

EFITSFSDGYDTVLGERGINLSGGQKQRISIARAFLRDTPFLLLDEATAN

LDTNSENMIKHALDNLIYKKTTIVIAHRISTIQNADQIVVLDQGEVSGFG

THDQLIKNNKLYQLLSNQQKMTS*

The present invention extends to host cells which are capable of producing the peptides/composition of the invention and/or containing the nucleic acid molecules described herein (which may have been transformed or transfected with a nucleic acid molecule and/or recombinant construct as described herein). When host cells are also to be transformed or transfected to contain ABC transporter and/or immune proteins the encoding sequences for these molecules may appear on the nucleic acid molecule and/or recombinant construct as described herein or may be provided on a separate nucleic acid molecule or recombinant construct.

Nucleic acid molecules may be introduced into a host cell by any appropriate means. Suitable transformation or transfection techniques are well described in the literature. A variety of techniques are known and may be used to introduce such vectors into prokaryotic or eukaryotic cells for expression. Preferred host cells for this purpose include insect cells, plant cells, eukaryotic cells and prokaryotic cells. In a preferred aspect the host cell is a microorganism. Preferred microorganisms are bacteria, such as lactic acid bacteria (e.g. *Lactobacillus kunkeei* or *Lactococcus garvieae*) or *E. coli*. Yeasts may also be used.

Thus the invention further provides a host cell selected from:

a) a host cell producing a composition as defined hereinbefore with the proviso that said composition is not a native product of said host cell; and b) a host cell containing a nucleic acid molecule of the invention as defined hereinbefore (including recombinant nucleic acid molecules of the invention) (e.g. in a recombinant construct as defined herein), wherein preferably said host cell produces a composition as defined hereinbefore. Preferred host cells according to a) are host cells which comprise a recombinant nucleic acid molecule of the invention. When the host cell contains a nucleic acid molecule of the invention (including a recombinant nucleic acid molecule of the invention), which may be in a recombinant construct of the invention, the composition and/or nucleic acid sequence on said construct may be native (or not native) to said host cell. In one embodiment the peptides may be overexpressed in their natural/native host cells. In a particularly preferred embodiment, the host cell (which may or may not be native) produces the Garvicin KS composition as described herein (or a variant thereof as described herein) and is preferably a *Lactococcus garvieae* cell.

In a particularly preferred embodiment the host cell produces garvicin KS and is a cell of the deposited strain of *Lactococcus garvieae* LMGT 1546 deposited at the VTT Culture Collection (Finland), on 4 Nov. 2015 and having Accession number VTT E-153488. Alternatively expressed the invention provides *Lactococcus garvieae* LMGT 1546 having Accession number VTT E-153488. The invention also extends to variants of this strain which result from further modification of the strain, e.g. by transformation.

The invention also extends to transformed or transfected prokaryotic or eukaryotic host cells containing a nucleic acid molecule, particularly a recombinant molecule, as defined above.

A further aspect of the invention provides a method of preparing a composition of the invention as hereinbefore defined, which comprises growing (e.g. culturing) a host cell as defined above, under conditions whereby said peptides of said composition are expressed and recovering said peptides thus produced. The peptides may be purified, e.g. as described hereinbefore. The expressed peptides form a further aspect of the invention.

Cells producing and secreting peptides of the invention, but which have been modified relative to native cells by expression of encoding nucleic acid material, form further aspects of the invention.

As described hereinafter, the compositions have particular utility in various therapeutic and prophylactic methods and uses. Host cells which produce the composition of the invention or peptides thereof may also be used for such purposes. The host cells may be in a more complex structure which may be used to prepare a composition or may be used directly for the claimed methods and uses. For example, if the host cell is a plant cell, plant material comprising the host cells may be generated and the plant material used for preparing compositions or used directly for the methods and uses of the invention. Plants, or plant parts or material comprising host cells of the invention form a further aspect of the invention.

To achieve the methods and uses of the invention the active ingredients, i.e. the peptide components of the composition or the host cell may be appropriately modified for use in a pharmaceutical or probiotic composition or a composition for use in preparing food products or other items or products. For example the composition or host cell used in accordance with the invention may be stabilized against degradation for example by the use of appropriate additives such as salts or non-electrolytes, acetate, SDS, EDTA, citrate or acetate buffers, mannitol, glycine, HSA or polysorbate.

Thus, the compositions or host cells may be provided in the form of a pharmaceutical composition comprising in addition one or more pharmaceutically acceptable diluents, carriers or excipients, which composition forms a further aspect of the invention and may be for use in therapy as described herein. Similar diluents, carriers or excipients may also be provided in compositions for non-pharmaceutical compositions but are not necessarily of pharmaceutical grade, e.g. for antibacterial protection of products. "Pharmaceutically acceptable" as referred to herein refers to ingredients that are compatible with other ingredients of the compositions or host cells (or products) as well as physiologically acceptable to the recipient. The invention also extends to compositions comprising multiple host cells (microorganisms) of the invention for use in methods described herein.

Conveniently the host cell or peptides may be provided as part of a probiotic composition. As referred to herein a "probiotic" is a live microorganism (a yeast or bacteria) that renders health benefits to the host when consumed in adequate quantities. For example, they may help in enhancing the microbial gut flora of the host and prevent proliferation of death-causing diseases. They may also help in reducing instances of gastrointestinal problems, enhance immunity of the consumer and improve skin and gut functionality. The host cell defined herein may be a probiotic, e.g. a lactic acid bacteria and thus provide a probiotic for uses as described herein. However, in a preferred aspect, the compositions of the invention may additionally comprise a probiotic microorganism which provides additional health benefits. In order to provide health benefits both the host cell and the probiotic microorganism are preferably live (as is preferred in other compositions of the invention), and remain capable of replication in the patient/subject after administration.

Thus, the invention also provides a probiotic composition comprising a composition or host cell (preferably microorganism) as defined herein, wherein said composition additionally comprises at least one probiotic microorganism (which is not a host cell (microorganism) of the invention). In a preferred aspect the probiotic microorganism is a lactic acid bacteria, preferably selected from the genus *Lactobacillus* or *Streptococcus*, preferably *Lactobacillus bulgaricus*, *Lactobacillus bifidus* and *Streptococcus thermophilus*.

The compositions described herein may be formulated in a conventional manner with one or more physiologically acceptable (where necessary) carriers, excipients and/or diluents, according to techniques well known in the art using readily available ingredients. Thus, the active ingredient may be incorporated, optionally together with other active substances as a combined preparation, with one or more conventional carriers, diluents and/or excipients, to produce conventional galenic preparations such as tablets, pills, powders (for topical administration or inhalation), lozenges, sachets, cachets, elixirs, suspensions (as injection or infusion fluids), emulsions, solutions, syrups, sprays, aerosols (as a solid or in a liquid medium), ointments, soft and hard gelatin capsules, suppositories, sterile injectable solutions, sterile packaged powders, and the like. Biodegradable polymers (such as polyesters, polyanhydrides, polylactic acid, or polyglycolic acid) may also be used for solid implants. The compositions may be stabilized by use of freeze-drying, undercooling or Permazyme.

Suitable excipients, carriers or diluents are lactose, dextrose, sucrose, sorbitol, mannitol, starches, gum acacia, calcium phosphate, calcium carbonate, calcium lactose, corn starch, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used.

The compositions may additionally include lubricating agents, wetting agents, emulsifying agents, viscosity increasing agents, granulating agents, disintegrating agents, binding agents, osmotic active agents, suspending agents, preserving agents, sweetening agents, flavouring agents, adsorption enhancers (e.g. surface penetrating agents or for nasal delivery, e.g. bile salts, lecithins, surfactants, fatty acids, chelators), browning agents, organic solvent, antioxidant, stabilizing agents, emollients, silicone, alpha-hydroxy acid, demulcent, anti-foaming agent, moisturizing agent, vitamin, fragrance, ionic or non-ionic thickeners, surfactants, filler, ionic or non-ionic thickener, sequestrant, polymer, propellant, alkalinizing or acidifying agent, opacifier, colouring agents and fatty compounds and the like.

The compositions of the invention may be formulated so as to provide quick, sustained or delayed release of the active ingredient after administration to the body by employing techniques well known in the art.

The composition may be in any appropriate dosage form to allow delivery or for targeting particular cells or tissues, e.g. as an emulsion or in liposomes, niosomes, microspheres, nanoparticles or the like with which the active ingredient may be absorbed, adsorbed, incorporated or bound. This can effectively convert the product to an insoluble form. These particulate forms may overcome both stability (e.g. degradation) and delivery problems.

These particles may carry appropriate surface molecules to improve circulation time (e.g. serum components, surfactants, polyoxamine908, PEG etc.).

The use of solutions, sprays, suspensions, gels and emulsions are preferred, e.g. the active ingredient may be carried in water, a gas, a water-based liquid, an oil, a gel, an emulsion, an oil-in water or water-in-oil emulsion, a dispersion or a mixture thereof.

Compositions may be for topical (i.e. to the skin or mucosal membranes), oral or parenteral administration, e.g. by injection. Injections may be used to provide systemic effects or to provide local effects at the site of infection, e.g. intramammary injection for mastitis.

Topical compositions and administration are however preferred, and include gels, creams, ointments, sprays, lotions, liniments, salves, sticks, soaps, powders, films, aerosols, drops, foams, solutions, emulsions, suspensions, dispersions e.g. non-ionic vesicle dispersions, milks and any other conventional pharmaceutical or cosmetic forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

Alternatively, the compositions may be provided in a form adapted for oral or parenteral administration. Alternative pharmaceutical forms thus include plain or coated tablets, capsules, suspensions and solutions containing the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof.

In view of the antibacterial properties of the compositions and host cells of the invention they may be used for therapeutic or prophylactic purposes. Thus, the present invention provides a composition or host cell (preferably microorganism) as defined hereinbefore for therapy. In particular the compositions and host cells may be use in treating or preventing bacterial infection. The compositions and host cells may be suitable for treating humans or for veterinary use.

Thus, in a further aspect the present invention provides a composition or host cell (preferably microorganism) as defined hereinbefore for use in treating or preventing a bacterial infection. Alternatively the invention provides use of a composition or host cell (preferably microorganism) as defined hereinbefore in the preparation of a medicament for treating or preventing a bacterial infection. Alternatively described the invention provides a method of treating or preventing a bacterial infection comprising administering a composition or host cell (preferably microorganism) as defined hereinbefore to a patient or subject. Furthermore, the present invention provides a product containing the peptides of the composition of the invention and optionally one or more additional active ingredients as a combined preparation for simultaneous, separate or sequential use in human or animal therapy, preferably as described herein. Also provided is a kit separately comprising each of the peptides of the composition of the invention, preferably for a use or method as described herein.

Preferably said kit (or product) is for simultaneous, separate or sequential use in a medical treatment or for prophylaxis as described herein.

As defined herein "treatment" (or treating) refers to reducing, alleviating or eliminating one or more symptoms of the bacterial infection which is being treated, relative to the symptoms prior to treatment. Such symptoms may be correlated with the abundance of bacteria present on the treated patient or subject. "Prevention" (or preventing or prophylaxis) refers to delaying or preventing the onset of the symptoms of the bacterial infection. Prevention may be absolute (such that no bacterial infection occurs) or may be effective only in some individuals or for a limited amount of time.

As referred to herein a "bacterial infection" is invasion of bodily tissue by a bacteria that proliferates at that site and which may result in injury to that tissue. Preferably the bacterial infection is a skin infection (preferably caused by *Staphylococcus*, e.g. by *Staphylococcus aureus*), an oral or throat infection (preferably caused by *Streptococcus*), an infection present in or causing dental caries (preferably caused by *Streptococcus*) or mastitis (preferably caused by *Staphylococcus* or *Streptococcus*).

In a particularly preferred aspect, the present invention provides a composition or host cell (preferably microorganism) as defined herein for use in treating or preventing mastitis in a milk-producing subject or patient, wherein preferably said subject or patient is a mammalian animal, preferably a human, cow, sheep, horse, pig or goat. As referred to herein a milk-producing animal refers to a lactating female mammalian animal, preferably a livestock animal.

Preferably the bacterial infection is caused by at least one bacteria selected from the genera *Bacillus, Streptococcus, Listeria, Enterococcus, Staphylococcus, Acinetobacter* and *Paenibacillus*, preferably selected from the species *Bacillus cereus, Listeria monocytogenes, Listeria innocua, Listeria grayi, Listeria seelingeri, Streptococcus thermophylus, Streptococcus agalactia, Streptococcus pneumonia, Strep-* tococcus salivarius, Enterococcus faecalis, Enterococcus faecium, Staphylococcus aureus, Acinetobacter baumanii, Acinetobacter nosocomialis and Paenibacillus larvae. In a particularly preferred aspect the bacterial infection is caused by at least one bacterial selected from Methicillin-resistant Staphylococcus aureus (MRSA), antimicrobial resistant (AMR) Acinetobacter baumanii, Vancomycin-resistant Entercocci (VRE) and antibiotic-resistant strains of Listeria monocytogenes.

Animals (or patients/subjects) to which the compositions or host cells may be applied or administered include mammals, reptiles, birds, insects and fish particularly during fish aquaculture (e.g. salmon or cod). Preferably the animals to which the compositions of the invention are applied are mammals, particularly primates, domestic animals, livestock and laboratory animals. Thus preferred animals include mice, rats, rabbits, guinea pigs, cats, dogs, monkeys, pigs, cows, goats, sheep and horses. Especially preferably the compositions are applied, or administered, to humans.

In a preferred aspect the composition comprises a host cell, preferably a lactic acid bacteria, preferably L. kunkeei, which is administered to the animal, which in a preferred aspect is a bee and the bacteria to be treated is Paenibacillus larvae. For convenience this may be administered in combination with food.

The administration may be by any suitable method known in the medicinal arts, including for example oral, parenteral (e.g. intramuscular, subcutaneous, intraperitoneal or intravenous), intestinal, percutaneous, buccal, rectal or topical administration or administration by inhalation. The preferred administration forms will be administered orally (e.g. in food for animals), or most preferably topically. As will be appreciated oral administration has its limitations if the active ingredient is digestible. To overcome such problems, ingredients may be stabilized as mentioned previously.

It will be appreciated that since the active ingredient for performance of the invention takes a variety of forms, e.g. a host cell (which may itself be contained in a more complex structure) or peptides, the form of the composition and route of delivery will vary. Preferably however liquid solutions, creams or suspensions would be employed, particularly e.g. for oral delivery or topical administration. In instances in which the host cell is provided in a more complex structure which itself may be ingested, the host cells may be ingested directly, e.g. plant material, or in a product prepared therefrom, e.g. an extract which may be solid or liquid.

The concentration of active ingredient in compositions of the invention, depends upon the nature of the compound used (i.e. the peptides or host cells), the mode of administration, the course of treatment, the age and weight of the patient/subject, the medical indication, the body or body area to be treated and may be varied or adjusted according to choice. Generally however, appropriate concentration ranges for the peptides of the composition (whether applied directly or assessed based on the production levels expected in vivo from host cells expressing the peptides) described herein are 0.0001, 0.0005, 0.001 or 0.01 to 25%, e.g. 0.0005-15%, e.g. 0.01 to 10%, such as 0.1 or 0.5 to 5, e.g. 1-5% (w/w of the final preparation for administration, particularly for topical administration, determined based on the total weight of all the peptides). Said concentrations are determined by reference to the amount of the peptides themselves and thus appropriate allowances should be made to take into account the purity of the composition. Effective single doses for peptides of the invention may lie in the range of from 0.1-100 mg/cm$^2$/day, preferably 0.1-10 mg/cm$^2$/day, when applied topically, depending on the animal being treated, taken as a single dose (again taking into account the total weight of the peptides used).

In a further aspect, the present invention provides use of a composition or host cell (preferably microorganism) as defined hereinbefore as an antibacterial. Preferably the antibacterial is effective against bacterial infection from a bacteria as described hereinbefore.

The antibacterial may be used to preserve food products to prevent their spoilage. Thus, in a further aspect, the present invention provides a method of preparing a preserved food product comprising adding a composition or a host cell (preferably microorganism) as defined hereinbefore to a food product. A "preserved" food product refers to a food product to which an antibacterial of the invention (i.e. a composition or host cell of the invention) has been applied to provide antibacterial (preservative) properties. A "food product" is an edible product that may be consumed by animals which provides nutritional benefits. Food products include in particular animal-derived food products, such as dairy and meat products as well as plant-derived food products. Various foods and beverages which may be susceptible to bacterial infection are contemplated. When host cells are to be added, these may be in the form of, for example, a plant or plant part containing those host cells and that plant, plant part or an extract thereof may be added to the food product, e.g. as an addition to a beverage which may also provide nutritional benefits, e.g. in sports drinks.

The invention thus further provides a preserved food product comprising a food product and a composition or a host cell (preferably microorganism) as defined hereinbefore.

The invention also provides a method of avoiding food spoilage comprising mixing a food product with a composition or a host cell (preferably microorganism) as defined hereinbefore. Food "spoilage" refers to a reduction in the nutritional properties, decay or bacterial infection of food. The food is mixed with the composition or host cells in appropriate proportions to provide beneficial antibacterial properties but without substantial deleterious effects on the taste or nutritional properties of the food product. Appropriate concentrations may be readily determined by methods known in the art.

The compositions and host cells of the invention may also be used to provide antibacterial properties to non-food items, e.g. medical products. Thus, in a further aspect the present invention provides an item covered, impregnated, or coated with a composition or a host cell (preferably microorganism) as defined hereinbefore. Preferably the item is a medical device, instrument, implement or equipment, a prosthetic or material, tissue or wound dressing. Medical devices include pacemakers and heart valves, medical implements include catheters and scalpels, medical equipment includes gloves and other clothing, prosthetics or material include artificial joints, breast implants and scaffold material. Wound dressings include plasters and bandages as well as cements, glues or matrices which may be used for wound repair.

The invention also provides a personal health care product (including cosmetic products) comprising a composition or a host cell as defined hereinbefore. The product may be a product which is susceptible to bacterial contamination or which may be used to provide antibacterial protection to the body to which it is applied. Thus, the health care products may be body, face or lip milks, foams, sprays, lotions, creams, gels or balms, make-up products (such as eye or face products, including eye shadow, powder, lipstick, foundation, mascara, blush, eyeliner, nail polish, tinted creams and foundations, sun make-up), creams, lotions or colourants, hair products such as hair rinse, spray mist, gel, mousse, shampoo, conditioner, lotion, emulsion or colouring product and oral health or dental products such as toothpaste, mouthwash, mouth gel or spray, lozenge or chewing gum.

Preferably the product is toothpaste, mouthwash, skin cream, lotion or spray.

The item or product is covered, impregnated, coated or mixed with the composition or host cells in appropriate proportions to provide beneficial antibacterial properties but without substantial deleterious effects on the item or product, e.g. its functional properties. Appropriate concentrations and methods of covering, impregnation or coating may be readily determined by methods known in the art.

A method of preparing the above described item or health care product comprising applying a composition or host cell of the invention to said item or product, or mixing or impregnating said item or product with said composition or host cell, forms a further aspect of the invention. The use of a composition or host cell of the invention to prepare such items or products is also considered an object of the invention.

The present invention also provides in vitro methods of killing, damaging or preventing the replication of bacteria comprising administering a composition or host cell (preferably microorganism) as defined hereinbefore to said bacteria. Relevant definitions for killing, damaging and preventing replication as provided hereinbefore are also relevant to this aspect of the invention.

The methods described in the Examples form further preferred aspects of the invention. All combinations of the preferred features described above are contemplated, particularly as described in the Examples. The invention will now be described by way of non-limiting Examples with reference to the drawings in which:

FIG. 1 shows A) the antimicrobial activity of nisin (Nis) and garvicin KS (KS) against important antibiotic-resistant strains of *Listeria* spp, vancomycin-resistant strains of *E. faecium* (VRE) and multi-resistant strains of *S. aureus* (MRSA). Discs containing antibiotics (penicillin, ampicillin, tetracyclin and vancomycin) were placed on lawns of the strains to be tested. For bacteriocin activity, bacteriocin producers were spotted in the first 5 plates while boiled culture of supematants were spotted in the last three plates. Proteinase K (+K) was added near to the spotted bacteriocins to demonstrate their proteinaceous nature. Proteinase sensitivity is seen when the inhibition zones are reduced. B) shows the antibacterial activity of garvicin KS, Cerein H (Huacin) and various antibiotics, as indicated on various *Acinetobacter* strains, as indicated in the figure.

FIG. 6 shows the sequences of related bacteriocin peptides and Aureocin A70.

EXAMPLES

Figure 1A:
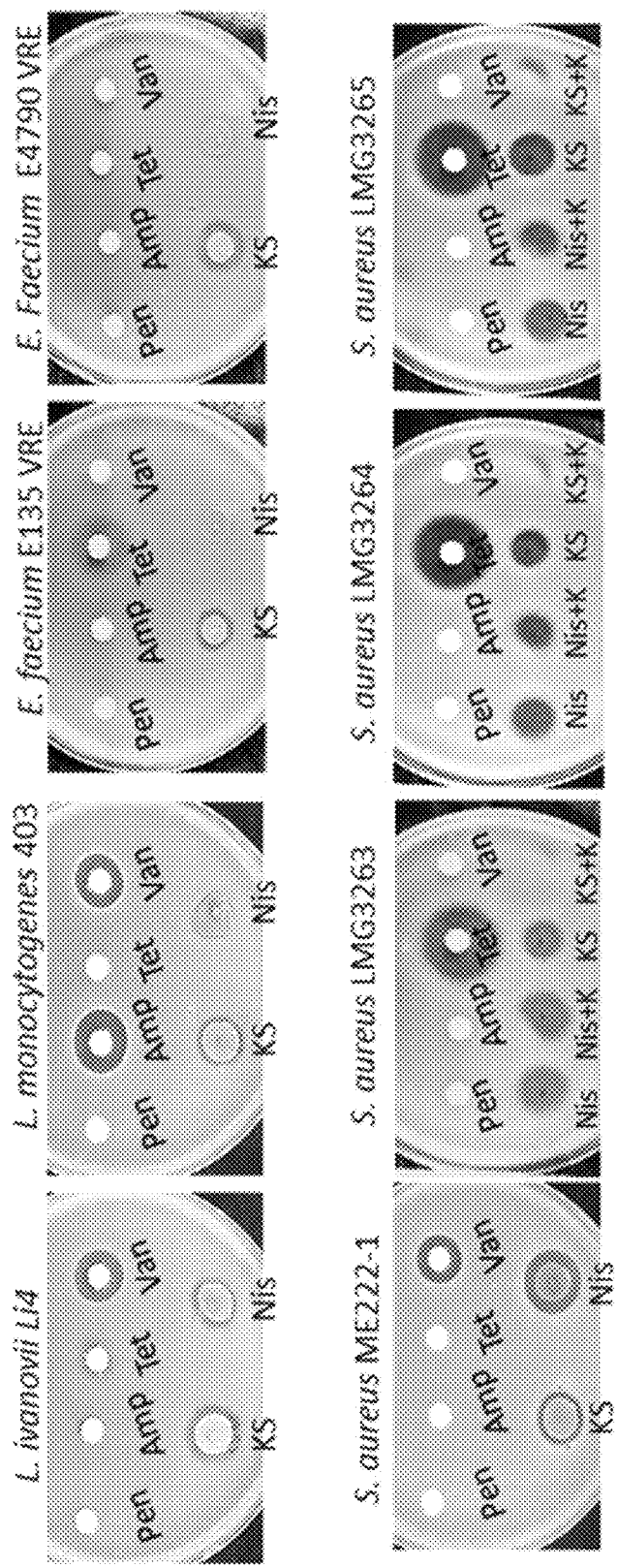

Example 1: Identification and Characterisation of Bacteriocin Garvicin KS

Materials & Methods Bacterial Strains and Growth Conditions

The bacterial collection of LAB which was used in the screening assay, was from raw milk samples collected from 221 farms in Kosovo from the period of November 2011 to June 2012 (Mehmeti et al., 2015, Food Control, 53, p 189-194). The large collection of LAB later was re-streaked out on de man, Rogosa, Sharpe (MRS) (Oxoid, UK) agar plates, single colonies were picked up and transferred into MRS broth tubes, and subsequently incubated at 30° C. for 24 h. The indicator strains were routinely grown in brain heart infusion (BHI) (Oxoid, UK) broth at 30° C. in aerobic condition. When appropriate, some indicator strains, like *Clostridium* species, were grown anaerobically in BHI broth at 37° C.

Screening for Broad-Spectrum Bacteriocin Producers

To screen for bacteriocin producers with broad inhibition spectra (BIS), *Lactococcus lactis, Lactobacillus sakei, Lactobacillus plantarum, Listeria innocua*, and *Staphylococcus aureus* from the food and dairy environment were used as indicators in the first round of screening. The antimicrobial screening was performed using the agar diffusion bioassay as previously described (Holo et al., 1991, J. Bacteriol., 173, p 3879-3887). Briefly, indicator cells from overnight cultures were diluted 100-fold in 5 mL of BHI soft agar and plated out as a lawn on BHI agar plates. Potential bacteriocin producers at volumes of 3 µL were spotted on the indicator lawn and then incubated at appropriate temperatures for 24 h for cell growth and cell inhibition. Inhibition was detected as clear zones around the spotted cells.

For protease-sensitivity, 2 µL of proteinase K at 20 µg/mL was applied near the spotted cells. Proteinase-sensitivity, seen as cell inhibition, was prevented close to where proteinase K was applied. Heat-sensitivity was assessed at 100° C. for 5 min before samples were tested for bacteriocin activity.

DNA Isolation, PCR, 16S rRNA Gene Sequencing and Rep-PCR

Total genomic DNA was isolated by using Fastprep (Bio101/Savant) and DNA mini kit (Omega Bio-tek Inc., GA). Amplification of 16S rRNA gene by PCR was carried out using the primers 5F (5'-GGTTACCTTGTTACGACTT-3', SEQ ID NO:24) and 11R (5'-TAACACATGCAAGTC-GAACG-3', SEQ ID NO:25) as previously described (Birri et al., 2013, Microbiol. Ecology, 65, p 504-516). PCR products were purified with NucleoSpin Extract II (Macherey-Nagel, Düren, Germany) and sent to GATC Biotech, Germany, for sequencing. For genetic fingerprinting, rep-PCR was performed using oligonucleotide primer $(GTG)_5$ (5'-GTGGTGGTGGTGGTG-3', SEQ ID NO:26) and the protocol as previously described (Mohammed et al., 2009, Int. J. Food Microbiol., 128, p 417-423). Amplicons were visualized under UV light after electrophoretic migration through a 1.0% agarose gel.

API Test-Fermentation Profiling

Carbohydrate fermentation was determined by using the API test according to the manufacturer's instructions (bioMerieuxesa, France). Colour changes were detected after 24 h at 30° C. Fermentation of a carbohydrate was confirmed when the colour in the medium changed from purple to yellow after 48 h.

Results

Screening for Broad Inhibition Spectrum Bacteriocins Producers

A large collection (1854 isolates) of LAB (Mehmeti et al., 2015, supra) were screened for BIS antimicrobials. In the first screening, we applied a panel of 5 genetically different indicators, with some being frequently found in milk (*L. lactis*), being normally associated with contaminated milk (*L. innocua, S. aureus*) and some being less common in dairy environment (*L. sakei* and *L. plantarum*). Dependent on the chosen indicators (Table 1), between 15-25% of the isolates were found to have antimicrobial activity, with the lowest score against the *L. plantarum* strain (273 out of 1854; 14.7%) while the highest scores were observed against the problematic bacteria *L. inocua* (467 out of 1854; 25. 2%) and *S. aureus* (402 out of 1854; 21.7%). Among the antimicrobial producers, 107 isolates could be considered as BIS producers because they were active against all these 5 different indicators.

TABLE 1

The portion of isolates producing antimicrobial activity against the five indicators

| Indicators | Isolates with antimicrobial activity[a] |
|---|---|
| *L. lactis* IL 1403 | 380 (20.5%) |
| *L. sakei* LMGT 2313 | 291 (15.7%) |
| *L. innocua* LMGT 2710 | 467 (25.2%) |
| *S. aureus* LMGT 3242 | 402 (21.7%) |
| *L. plantarum* LMGT 2003 | 273 (14.7%) |
| All five[b] | 107 (12.5%) |

[a]Total isolates screened for antimicrobial activity were 1854
[b]Number of isolates with antimicrobial activity against all the five indicators concurrently To avoid identification of known or related bacteriocins such as nisin, lactococcins G, A, B and M produced by dairy-associated lactococci, we used characterized lactococcal producers of these bacteriocins as indicators for the next round of screening. Our rational was that these bacteriocin-producing indicators would be immune to other producers of the same or related bacteriocins due to dedicated immunity and cross immunity mechanisms (Jack et al., 1995, Microbiological Reviews, 59, p 171-200). Among the 107 BIS isolates, only fourteen of these were found to be capable of killing all these bacteriocin producing lactococcal indicators (data not shown). Subsequent physicochemical analysis confirmed that the antimicrobial activity from these fourteen isolates had typical bacteriocin characteristics, i.e., being sensitive to proteinase K and heat-stable.

The fourteen isolates were subsequently genotyped by 16S rDNA gene sequencing. The sequencing results revealed that ten of these showed 100% sequence identity to *L. garvieae* while the remaining four showed highest sequence identity to *E. faecalis* (over 98%).

Characterization of the Ten Bacteriocin Producing *L. garvieae* Isolates

The ten *L. garvieae* isolates selected were from 10 different farms of 4 geographically different regions in Kosovo: Gjakova (2 isolates), Rahoveci (4 isolates), Skenderaji (2 isolates) and Sharri (2 isolates) (Mehmeti et al., 2015, supra). During the inhibition assay described above, it was noticed that the ten *L. garveae* isolates had identical inhibition spectra, indicating that they might produce the same bacteriocin(s) and hence possibly have the same genetic background. To assess their genetic similarity, rep-PCR was performed. As control, *L. garveae* DCC 43, which is the producer of the known bacteriocin garvicin ML and was isolated from the intestine of Mallard duck (Borrero et al., 2011, supra), was used. All ten *L. garvieae* isolates from Kosovo appeared to have the same patter of amplified DNA bands but this pattern was different from that of DCC 43 (data not shown). In addition, the ten *L. garvieae* isolates also shared the same fermentation profile of different sugars tested (Table 2). In the fermentation profile, all ten Kosovo-derived *L. garvieae* isolates gave positive signals on the same 18 sugars tested while the DCC 43 strain gave positive signals only on 13 of them. Further, all of these 13 sugars fermented by DCC 43 were within the list of the 18 fermentable sugars for the Kosovo isolates, indicating that the dairy-derived isolates have a much larger fermentation capacity than the Mallard-duck gut-derived DCC 43. It is also noteworthy that the sugars lactose, galactose and sucrose which are common in milk were fermented by the Kosovo-derived isolates but not by DCC 43, thus providing strong evidence that the growth of the Kosovo-derived isolates are adapted to dairy environments while DCC 43 is not. As the ten Kosovo-derived isolates appear identical in terms of inhibition spectra, fermentation profiles, and genetic profiles by rep-PCR, it was considered likely that they were very similar, if not identical, genetically and present the same bacteriocin activity. Therefore, only one of them, termed L *garvieae* KS 1546, was assessed further. This strain has been deposited at the VTT Culture Collection (Finland), on 4 Nov. 2015 and has Accession number VTT E-153488.

TABLE 2

Fermentation profile of the ten[a] dairy-derived bacteriocin producers of *L. garvieae* from Kosovo compared with that of the gut-derived *L. garvieae* DCC 43

| Active ingredients | KS 1564[a] | DCC 43 |
|---|---|---|
| Control group | −[b] | − |
| Glycerol | − | − |
| Erythritol | − | − |
| D-arabinose | − | − |
| L-arabinose | − | − |
| Ribose | + | + |
| D-xylose | − | − |
| L-xylose | − | − |
| Adonitol | − | − |
| β-methyl-D-xyloside | − | − |
| Galactose | + | − |
| D-glucose | + | + |
| D-fructose | + | + |
| D-mannose | + | + |
| L-sorbose | − | − |
| Rhamnose | − | − |
| Dulcitol | − | − |
| Inositol | − | − |
| Mannitol | + | − |
| Sorbitol | − | − |
| α-methyl-D-mannoside | − | − |
| α-methyl-D-glucoside | − | − |
| N-acetyl-glucoside | + | + |
| Amygdalin | + | + |
| Arbutin | + | + |
| Esculin | + | + |
| Salicin | + | + |
| Cellobiose | + | + |
| Maltose | + | + |
| Lactose | + | − |
| Melibiose | − | − |
| Sucrose | + | − |
| Trehalose | + | + |
| Inulin | − | − |

TABLE 2-continued

Fermentation profile of the ten[a] dairy-derived bacteriocin producers of *L. garvieae* from Kosovo compared with that of the gut-derived *L. garvieae* DCC 43

| Active ingredients | KS 1564[a] | DCC 43 |
|---|---|---|
| Melezitose | − | − |
| D-raffinose | − | − |
| Starch | − | − |
| Glycogen | − | − |
| Xylitol | − | − |
| β-gentiobiose | + | + |
| D-turanose | − | − |
| D-lyxose | − | − |
| D-fuccose | − | − |
| L-fuccose | − | − |
| D-arabitol | − | − |
| L-arabitol | − | − |
| Gluconate | + | − |
| Potassium 2-ketogluconate | − | − |
| Potassium 5-ketogluconate | − | − |

[a]All ten *L. garveae* isolates from Kosovo had the same fermentation profile. Therefore only, KS 1546, is shown here
[b]"−" means no fermentation while "+" means fermentation detected A more extended comparison between the bacteriocin activity of *L. garvieae* KS 1546 (termed garvicin KS) and *L. garvieae* DCC 43 (garvicin ML producer) can also be seen in Table 3. Amongst the 53 strains of different genera in the Firmicutes family tested, garvicin KS showed remarkable antimicrobial activity against all of them (100%; n=53) while the sensitive portion was about 74% (n=39) for garvicin ML producer. We also noticed that garvicin KS was more potent (i.e., relatively lower MIC values) than garvicin ML toward several genera of known pathogens, including *Enterococcus*, *Listeria* and *Staphylococcus*.

TABLE 3

Comparison of the inhibitory spectra of *L. garvieae* KS 1546 with *L. garvieae* DCC 43

| | Relative MIC value[a] | |
|---|---|---|
| Indicators | KS 1546 | DCC 43 |
| *Bacillus cereus* LMGT 2805 | 128-256 | 64 |
| *Clostridium bifermentans* LMGT 2519 | 64-128 | 16-32 |
| *C. sporogenes* LMGT 2515 | 256 | 32-64 |
| *C. tyrobutyricum* LMGT 2511 | 128 | 32 |
| *C. tyrobutyricum* LMGT 2524 | 128 | 32-64 |
| *Coronobacterium pisciola* LMGT 2332 | 8-16 | NI[b] |
| *Enterococcus avium* LMGT 3465 | ≤0.25 | ≤0.25 |
| *E. faecalis* LMGT 2333 | 8-16 | 64-128 |
| *E. faecium* LMGT 2763 | 4-8 | 32-64 |
| *E. faecium* LMGT 2772 | ≤0.25 | 32 |
| *E. faecium* LMGT 2783 | 8-16 | 64 |
| *E. faecium* LMGT 2876 | 16-32 | 64-128 |
| *Lactobacillus curvatus* LMGT 2353 | 16 | 16 |
| *L. curvatus* LMGT 2355 | 16 | 2-4 |
| *L. curvatus* LMGT 2371 | 8-16 | 32 |
| *L. curvatus* LMGT 2715 | 128 | 32 |
| *L. plantarum* LMGT 2003 | 16 | 64 |
| *L. plantarum* LMGT 2352 | 16 | 16 |
| *L. plantarum* LMGT 2357 | 32 | 64 |
| *L. plantarum* LMGT 2358 | 8 | 512 |
| *L. plantarum* LMGT 2362 | 64 | NI |
| *L. plantarum* LMGT 2379 | 16-32 | 32 |
| *L. plantarum* LMGT 3125 | 16 | NI |
| *L. Sakei* LMGT 2361 | 64 | 32 |
| *L. Sakei* LMGT 2380 | 64-128 | 32 |
| *L. Sakei* LMGT 2799 | 32 | 8-16 |
| *L. salivarius* LMGT 2787 | 64-128 | NI |
| *Lactococcus garvieae* LMGT 3390 | 16 | NI |
| *L. lactis* IL1403 | 1 | 1 |
| *L. lactis* LMGT 2081 | 1-2 | ≤0.25 |
| *L. lactis* LMGT 2130 | 16-32 | 8 |
| *L. lactis* LMGT 2705 | 4-8 | ≤0.25 |
| *L. lactis* LMGT 3419 | 8 | ≤0.25 |
| *Leuconostoc gelidium* LMGT 2386 | 128-256 | 32-64 |
| *Listeria innocua* LMGT 2710 | 16 | 32 |
| *L. innocua* LMGT 2785 | 8-16 | 32 |
| *L. ivanovii* LMGT 2813 | 64 | 32 |
| *L. monocytogenes* LMGT 2604 | 32 | 32 |
| *L. monocytogenes* LMGT 2650 | 32-64 | 64 |
| *L. monocytogenes* LMGT 2651 | 32-64 | NI |
| *L. monocytogenes* LMGT 2652 | 128-256 | NI |
| *L. monocytogenes* LMGT 2653 | 128-256 | NI |
| *Pediococcus acidilactici* LMGT 2002 | 64 | 32 |
| *P. pentosaceus* LMGT 2001 | 128 | 16-32 |
| *P. pentosaceus* LMGT 2366 | 256-512 | 64 |
| *Staphylococcus aureus* LMGT 3022 | 256 | 512 |
| *S. aureus* LMGT 3023 | 256 | NI |
| *S. aureus* LMGT 3242 | 128 | NI |
| *S. aureus* LMGT 3262 | 256 | NI |
| *S. aureus* LMGT 3263 | 256 | NI |
| *S. aureus* LMGT 3264 | 128-256 | NI |
| *S. aureus* LMGT 3265 | 128 | ≥512 |
| *Streptococcus salivarius* B 1301 | 64 | NI |

[a]Minimum inhibition concentration (MIC) was defined as the minimum amount of bacteriocin that inhibited at least 50% of the growth of the indicator in 200 μL of culture. The relative MIC value is relative to the MIC value for the indicator *L. lactis* IL 1403. Hence, the MIC value of *L. lactis* IL 1403 was referred to as 1 while MIC values of other indicators were relative to that of *L. lactis* IL 1403
[b]"NI" means no inhibition activity in the conditions tested Antimicrobial Activity Against Problematic or Potentially Problematic Bacteria As the antimicrobial activity of garvicin KS is relatively broad, we explored further its potential to kill a larger panel of important pathogens. The list contained 147 problematic or potentially problematic bacteria of species belonging to *Listeria*, *Staphylococcus*, *Streptococcus* and *Enterococcus*, isolated from food and clinical sources. In this assay, we compared the antimicrobial activity of garvicin KS with that of garvicin ML and nisin, the last one being known as a broad inhibition-spectrum bacteriocin (AIKhatib et al., 2014, PLOS One 9:e102246 doi:10.1371/journal-.pone.0102246). In general, garvicin ML was much less active compared to nisin and garvicin KS (Table 4): among the 147 strains tested, only 51 strains (34.6%) were killed by garvicin ML while 112 strains (76.1%) by nisin and remarkably, 139 strains (94.6%) by garvicin KS. At genus and species level, only against *E. faecium* was garvicin ML more active than nisin (7/7 for garvicin ML and 3/7 for nisin) but it was equally as active as garvicin KS (7/7). Otherwise, garvicin ML was much less active toward any of the other species. In all cases, garvicin KS was either equal or better than nisin, regardless of whether the isolates were from clinical or food environments, except for the activity toward clinical isolates of *S. aureus* where nisin appeared marginally better (24/25 for nisin and 23/25 for KS).

TABLE 4

Comparison of the antimicrobial activity of garvicin KS with that of Nisin and garvicin ML, against problematic bacteria

| | Original sources[b] | | | | | |
|---|---|---|---|---|---|---|
| | Clinical | | | Food | | |
| Indicators[a] | Nisin | DCC 43 | KS 1546 | Nisin | DCC 43 | KS 1546 |
| L. monocytogenes (n = 24) | 4/4 | 0/4 | 4/4 | 20/20 | 0/20 | 20/20 |
| L. innocua (n = 6) | — | — | — | 6/6 | 1/6 | 6/6 |
| L. grayi (n = 2) | — | — | — | 2/2 | 0/2 | 2/2 |
| L. seelingeri (n = 1) | — | — | — | 1/1 | 0/1 | 1/1 |
| Staph. Aureus (n = 53) | 24/25 | 9/25 | 23/25 | 18/28 | 4/28 | 27/28 |
| Strep. Thermophylus (n = 8) | — | — | — | 8/8 | 8/8 | 8/8 |
| S. agalactia (n = 1) | 1/1 | 1/1 | 1/1 | — | — | — |
| S. pneumonia (n = 2) | 1/1 | 1/1 | 1/1 | 1/1 | 1/1 | 1/1 |
| S. salivarius (n = 1) | 1/1 | 1/1 | 1/1 | — | — | — |
| E. faecalis (n = 42) | 0/2 | 0/2 | 2/2 | 22/40 | 18/40 | 35/40 |
| E. faecium (n = 7) | — | — | — | 3/7 | 7/7 | 7/7 |
| Total (n = 147) | 31/34 | 12/34 | 32/34 | 81/113 | 39/113 | 107/113 |

[a]The numbers in parentheses are the number of strains tested, e.g., for L. monocytogenes, 24 strains were tested, of which 4 and 20 strains are from clinical and food sources, respectively
[b]The numerators are the number of strains which are sensitive while the denominators are the number of strains tested, e.g., 4 strains of L. monocytogenes from clinical sources were tested; all 4 were sensitive to nisin and garvicin KS (KS) but none to garvicin ML (DCC 43)

Garvicin KS was also able to kill Gram negative bacteria, including all 5 tested strains of *Acinetobacter baumanii*, both tested strains of *A. nosocomialis* as well as 12 other tested strains of *Acinetobacter* (*A. pittii, A. ursingii, A. gen, A. soli, A. radioresistens, A. towneri, A. calcoaceticus* and *A. iwoffii*) (data not shown). This is in contrast to known bacteriocins which are not active against *A. baumanii* (which thus forms a preferred positive feature of the claimed bacteriocins).

Activity Against Antibiotic Resistant Bacteria

Use of antibiotics is a common practice in many farms in Kosovo that has resulted in a relatively high prevalence of antibiotic resistant bacteria. The most commonly used antibiotics in Kosovo are penicillin, streptomycin, oxitetracyclin and ampicillin, the first two normally in combination as a mixture known as PenStrep. To examine whether garvicin KS can kill strains of methicillin-resistant *S. aureus* (MRSA; a causative of mastitis) and antibiotic-resistant strains of *L. monocytogenes* (an important food-borne pathogen) and vancomycin-resistant *E. faecium* (VRE), a test on agar plates was performed. Discs containing antibiotics (penicillin, ampicillin, tetracyclin and vancomycin) at concentration of 1 mg/mL were placed on lawns of the strains to be tested. For bacteriocin activity, 3 µL of bacteriocin producers were spotted in the first 5 plates while boiled culture of supematants (3 µL) were spotted in the last three plates. Proteinase K (2 µL) (+K) was added near to the spotted bacteriocins to demonstrate their proteinaceous nature. Proteinase sensitivity is seen when the inhibition zones are reduced. As depicted in FIG. 1A, these antibiotic resistant strains were sensitive to garvicin KS and to some extent, also to the control nisin.

Figure 1B:
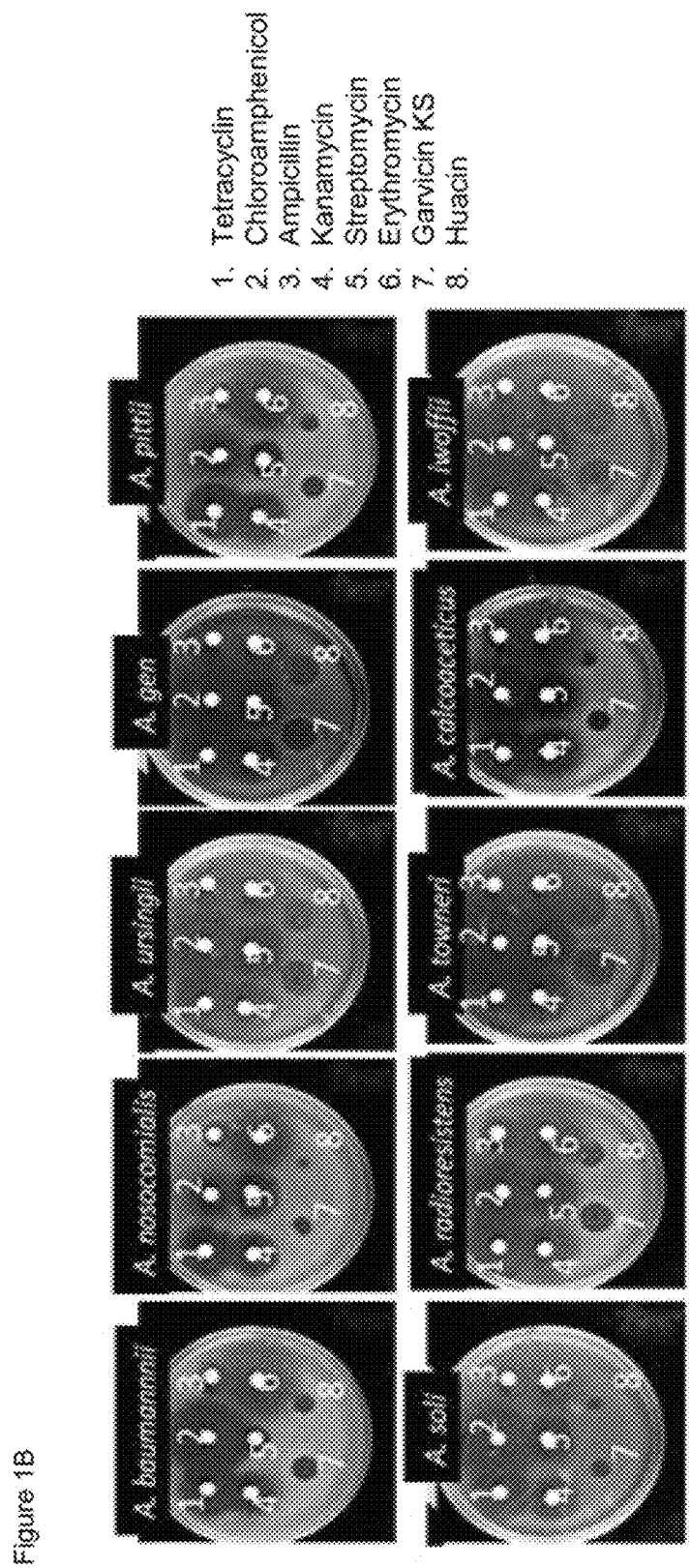

A similar study was performed on *Acinetobacter* strains using tetracyclin, chloramphenicol, ampicillin, kanamycin, streptomycin, erythromycin, Garvicin KS and Cerein H. Both Garvicin KS and Cerein H (shown as Huacin) showed activity against all the tested strains (FIG. 1B).

CONCLUSION

Garvicin KS has properties typical for most bacteriocins, i.e., heat stability and proteinase sensitivity. However, the bacteriocin activity of garvicin KS is much broader compared to most known bacteriocins.

Garvicin KS is a BIS bacteriocin with an inhibition spectrum containing many important problematic bacteria of genera *Listeria, Staphylococcus, Streptococcus* and *Enterococcus*. The broadness of inhibition is comparable to that of nisin which has been approved by FAO/WHO for use as a food preservative in many countries (Paul Ross et al., 2002, Int. J. Food Microbiol., 79, p 3-16). Like nisin, garvicin KS was also capable of killing antibiotic-resistant bacteria of *L. monocytogenes*, MRSA and VRE which are common problematic bacteria in dairy environments and/or hospital environments (and in most cases outperformed nisin). As such, garvicin KS has a great potential as a preservative or an antimicrobial in applications dealing with pathogens and food spoilage bacteria.

Example 2: Characterization of Garvicin KS and Related Bacteriocins and Peptide Substitution Effects on Activity Materials and Methods Bacterial Strains and Growth Conditions The bacteriocin-producing strain *Lactococcus garvieae* LMGT 1546 (identified in Example 1) was isolated from raw milk in a Kosovo milk farm (Example 1). The strain was grown overnight in M17 medium (Oxoid) supplemented with 0.5% (wt vol$^{-1}$) glucose at 30° C. without shaking. *L. garvieae* LMGT 1356, *L. monocytogenes* LMGT 319, *E. faecium* LMGT 2763 and *L. lactis* IL1403 were grown at the same conditions. *B. cereus* LMGT 2805 was grown at 37° C. with agitation. *L. lactis* IL1403 was used as an indicator for the bacteriocin activity during all the purification steps.

Bacteriocin Assays

The bacteriocin activity was assayed using a microtitre plate assay (Holo et al., 1991, supra). The plates were incubated at 30° C. for 8 h and the growth was measured spectrophotometrically at 600 nm ($A_{600}$) with 15 min intervals using SPECTROstarNano (BMG LABTECH, Germany). The MIC was defined as the minimal bacteriocin concentration that inhibited the growth of the indicator strain by at least 50% (50% of the turbidity of the control culture without bacteriocin) in 200 µl culture. MIC is equal to one bacteriocin unit (BU).

Purification of GarvK

GarvK was purified from the supernatant of one liter of *Lactococcus garvieae*. The cells were grown to the early stationary phase and bacteria were removed by centrifugation at 10,000×g for 15 min. The bacteriocin was precipitated from the culture with ammonium sulfate (45% saturation) at 4° C. and harvested by centrifugation (15,000×g, 4° C., 30 min). The protein pellet which yielded crude bacteriocin was dissolved in 100 ml of water+0.1% (v/v) trifluoroacetic acid (TFA), Sigma-Aldrich (buffer A). The sample was applied to a HiPrep 16/10 SP-XL column (GE Healthcare Biosciences) equilibrated with buffer A. The column was washed with 100 ml of 10 mM sodium phosphate buffer at pH 6.8 before elution of the bacteriocin with 50 ml of 0.2 M NaCl. The eluate was applied to a Resource RPC column (1 ml) (GE Healthcare Biosciences) connected to a fast protein liquid chromatography (FPLC) system (Amersham Pharmacia Biotech). A linear gradient of isopropanol (Merck) in aqueous 0.1% (vol/vol) TFA (buffer B) at the flow rate of 1.0 ml min$^{-1}$ was used for elution. The crude bacteriocin was eluted in two peaks with 31 and 34% of buffer B respectively. Since the second (34% of isopropanol) peak fractions were more active, they were chosen for further purification. Active fractions of the second peak were diluted in buffer A five times and applied to a RPC C8 column (Amersham Biosciences). Pure bacteriocin was eluted with 36% of buffer B. Fractions showed antibacterial activity were chosen for mass spectrometry analysis.

Mass Spectrometry Analysis

Acquisition of MS data was performed on an Ultraflex MALDI-TOF/TOF (Bruker Daltonics, Bremen, Germany) instrument operated in reflection mode with delayed extraction. Positively charged ions in the m/z range of 200 to 6000 were analyzed using an acceleration voltage of 25 kV. The sample spectra were calibrated externally with a calibration standard covering the m/z range 700-3100 (Bruker Daltonics, Bremen Germany). The two most pure active fractions after the second RPC step (C8 column) were chosen for Edman degradation analysis.

Protein Sequence Analysis of GarvK and Identification of the Structural Genes

The N-terminal amino acid sequence of the purified bacteriocin was determined by Edman degradation using an ABI Procise 494 sequencer (Alphalyse, Denmark).

Synthetic Peptides

All the peptides in the experiments were synthesized by Pepmic Co., LTD, China with 90-99% purity except for CerHA, CerHB and CerVC (85% purity). Aureocin A70F is almost identical to bacteriocin AureocinA70, both being made up of four peptides (peptide A, B, C and D) but in peptide D of Aureocin A70F leucine 29 is replaced with phenylalanine (EWU40578.1). Synthesized peptides were solubilized to a concentration of 0.1 to 10 mg/ml in 0.1% (vol/vol) trifluoroacetic acid and stored at −20° C. until use.

Substitution Assays

Substitution assays were performed to see if related peptides from different bacteriocins or peptides from Aureocin A70 could replace each other functionally. The peptides examined were from Cerein H (CerHA, CerHB, CerHC, CerHD), Cerein X (CerXA, CerXB, CerXC), Cerein V (CerVA, CerVB, CerVC), Aureocin A70 (A70A, A70B, A70C, A70D) and Garvicin KS (GarKosA, GarKosB, GarKosC). All the peptides were used at the same concentrations (0.1 mg/ml) and equal volumes of single peptides were used to create bacteriocin mixtures. In total 21 substitution assays were performed. The following combinations were used:

i) (CerHA or CerHB or CerVC)+GarKosB+GarKosC;
ii) (CerHC or CerXB or CerVB or A70B)+GarKosA+GarKosC;
iii) GarKosA+GarKosB+CerVA;
iv) (GarKosB or A70B or CerVB or CerXB)+CerHA+CerHB+CerHD;
v) CerVC+CerHC+CerHD;
vi) GarKosA+CerHC+CerHD;
vii) CerVA+CerHA+CerHB+CerHC;
vii) (GarKosB or CerHC or CerXB or CerVB)+A70A+A70C+A70D;
ix) GarKosC+A70B+A70C+A70D;
x) CerVA+CerXB+CerVC.

Results

Purification and Characterization of a Garvicin Kosovo Peptide.

Figure 2:
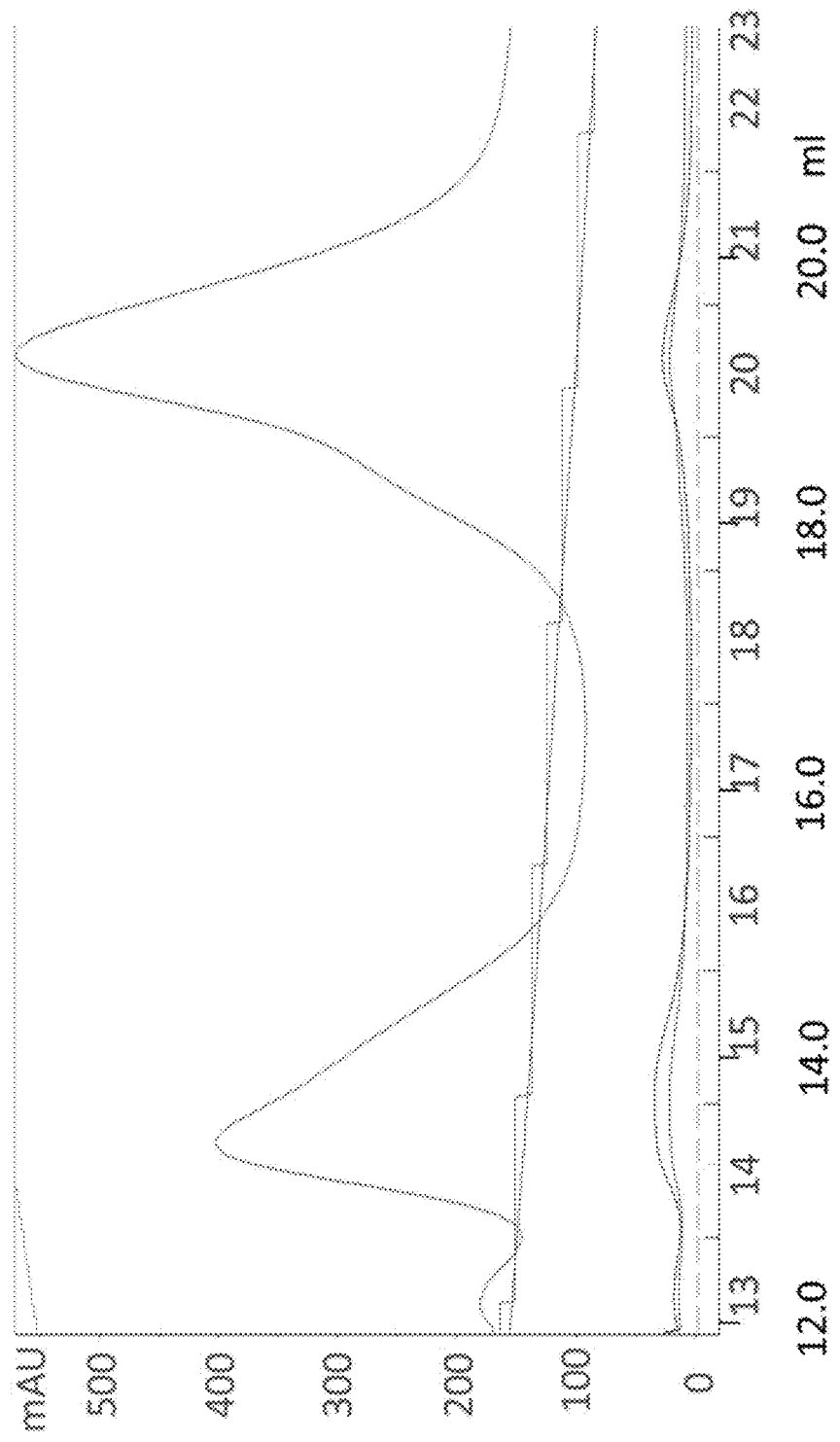
FIG. 2 shows the elution profile of Garvicin KS with 2-propanol in the first RPC step.

Purification was accomplished by established methods for bacteriocins that include cation exchange chromatography followed by two reverse phase chromatography steps (RPC). In the first RPC two peaks of antimicrobial activity were identified that corresponded with peak's absorbance at 280 nm (FIG. 2). The first peak of activity (Peak 1) was eluted at 31% 2-propanol and the second (Peak 2) at 34%. MS analysis of the peaks' fractions revealed several predominant masses from about 3000 to 3500 Da (FIG. 3 a,b) in both of them. Activity spectra of the peaks were similar (data not shown), but since Peak 2 encompassed most antimicrobial activity, it was consequently chosen for further analysis.

Figure 4:
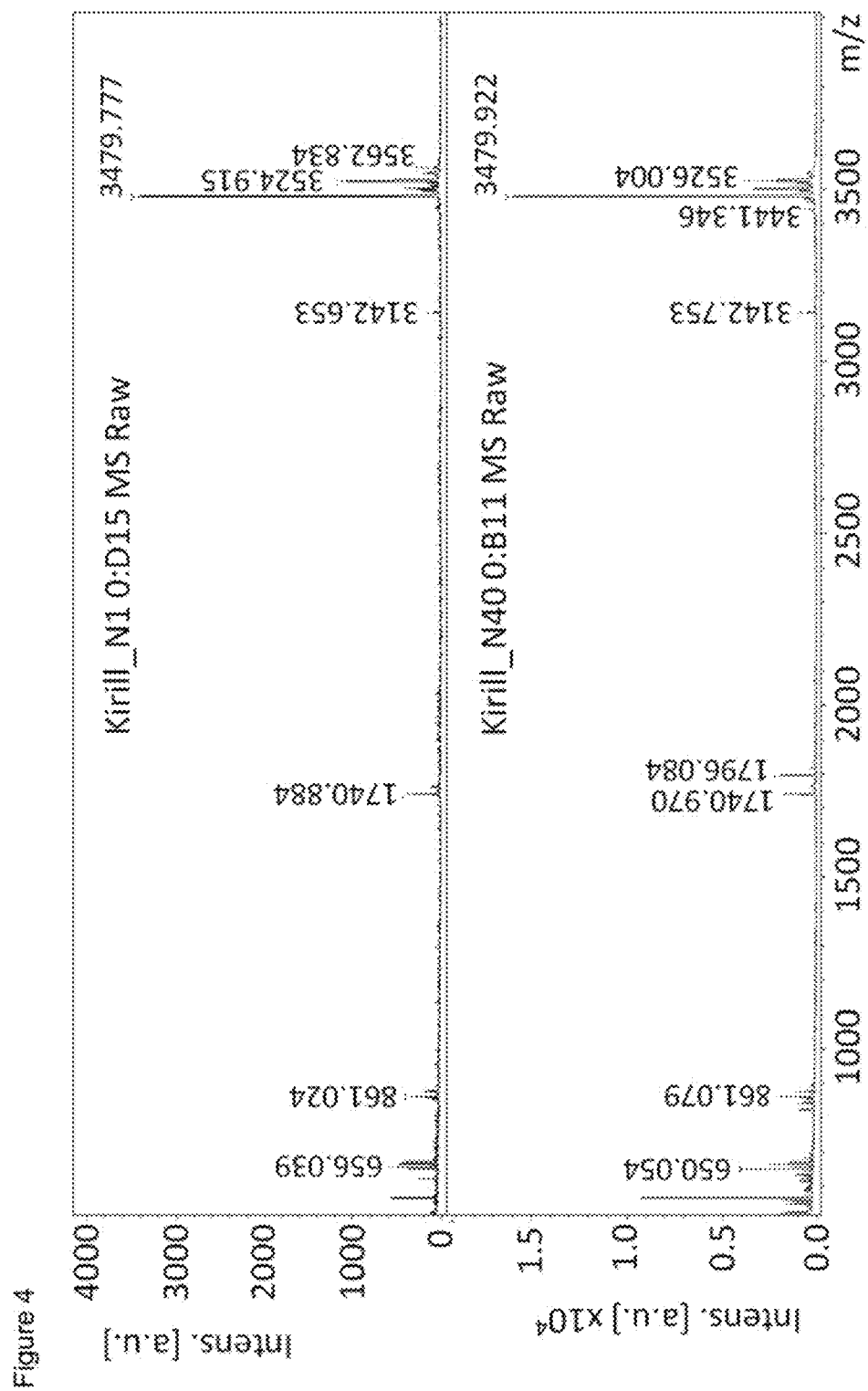
FIG. 4 shows the results of MS of the samples (fractions 40 and 41) for amino acid sequencing after the second RPC step.
Figure 5B:
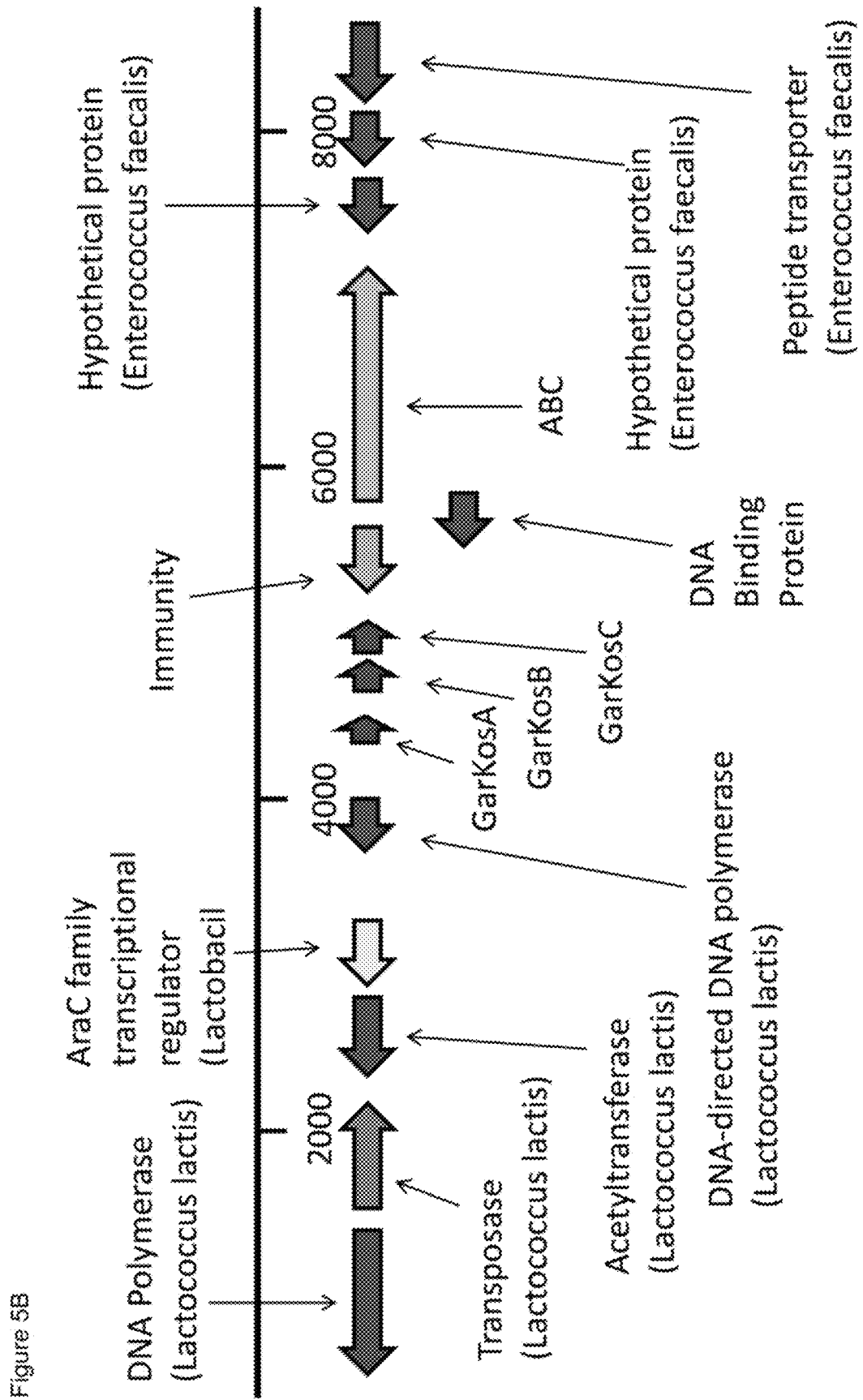
FIG. 5 shows a) the peptide sequences of the Garvicin Kosovo (Garvicin KS) peptides, and b) operon maps of Kosovo family bacteriocin producers.
Figure 5B:
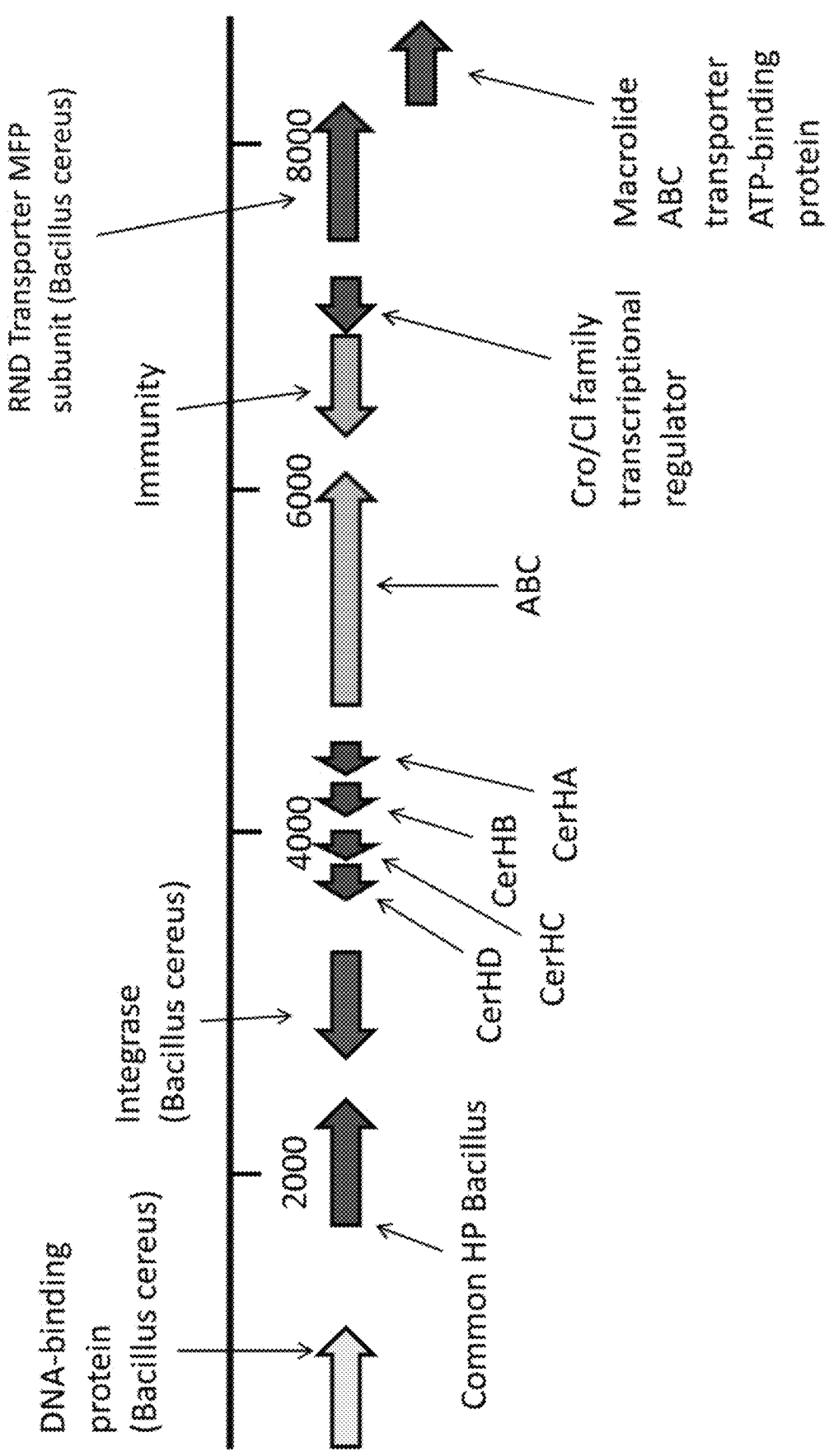
Figure 5B:
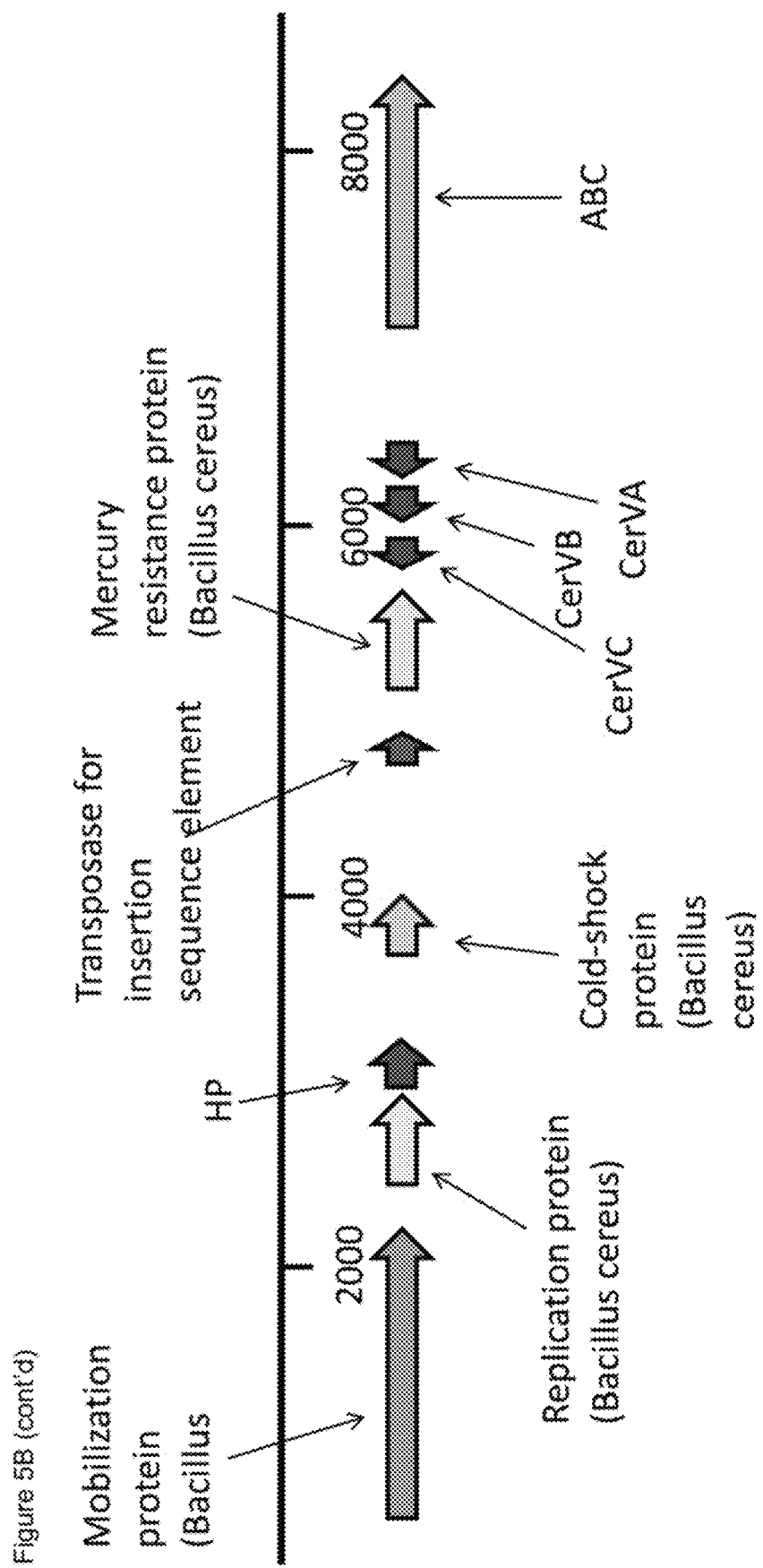
Figure 5B:
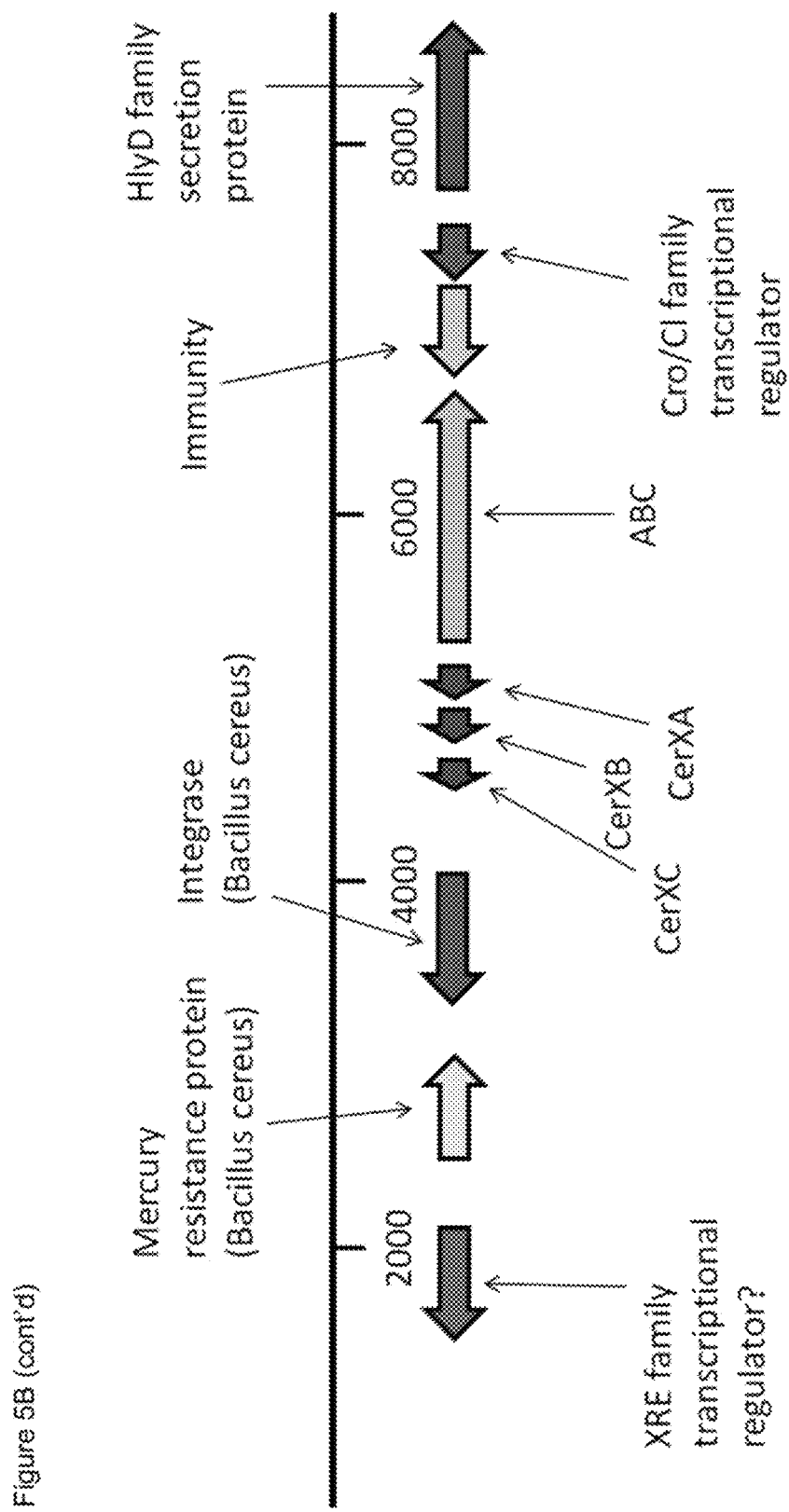
Figure 5B:
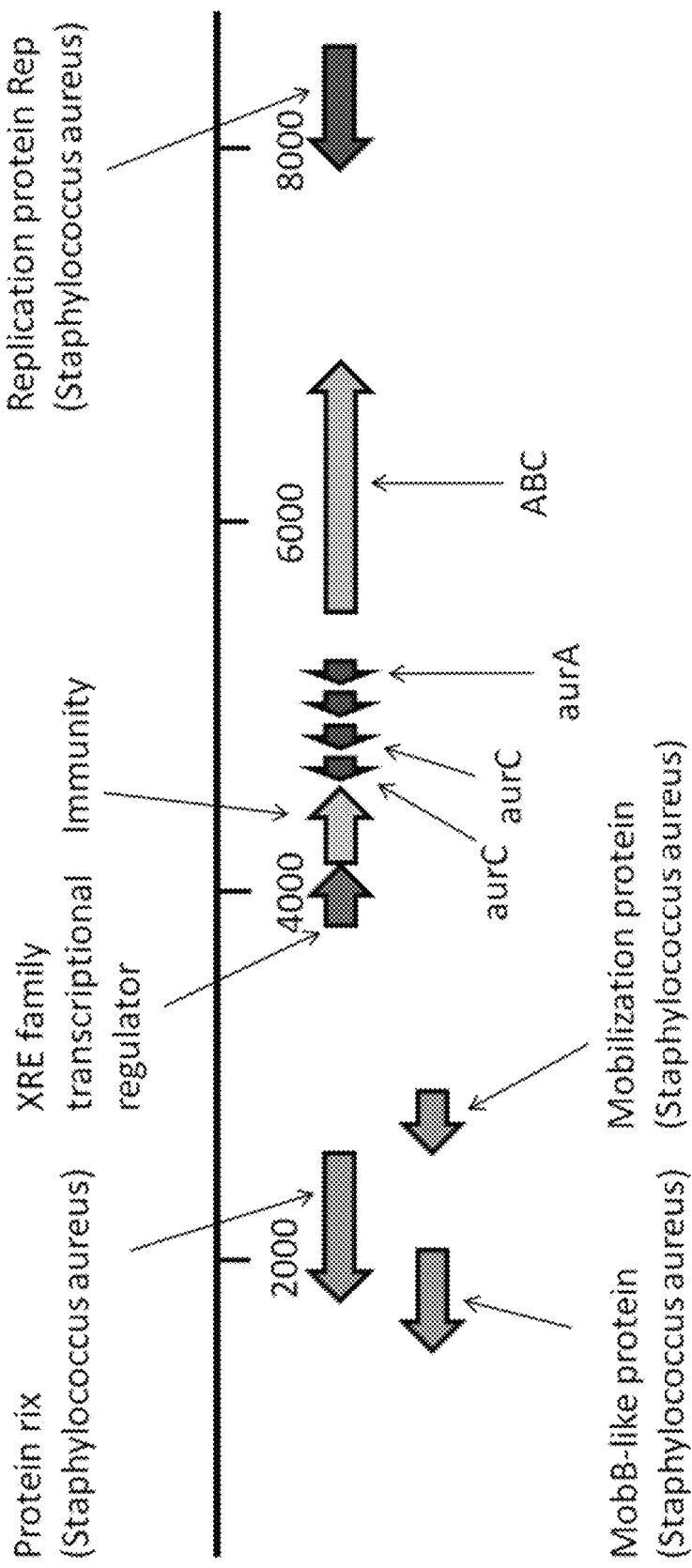

In the second RPC of Peak 2 significant loss of bacteriocin activity was observed and the active fractions were obtained at 36% 2-propanol, with a final yield of only 0.3% of the starting activity (Table 5). MS analysis of the two most active fractions (fractions 40 and 41) showed that both contained an identical predominant peptide mass of 3479.9 Da (FIG. 4). Subsequent N-terminal amino acid sequencing by Edman degradation revealed an identical amino acid sequences of 20 residues in both samples: MGAIIKA-GAKIVGKGVLGGG (N-terminal sequence of SEQ ID NO:1).

TABLE 5

Purification of Garv Kos 1L

| Fraction | Volume (ml) | Total activity (10$^4$ BU) | Yield (%) |
|---|---|---|---|
| Culture supernatant | 1000 | 63 | 100 |
| Ammonium sulfate precipitate | 100 | 51 | 81 |
| Cation-exchange chromatography | 50 | 26 | 41 |
| Reverse-phase chromatography HiPrep | 5 | 10 | 16 |
| Reverse-phase chromatography C8 | 5 | 0.2 | 0.3 |

Identification of Multiple Peptides and a Bacteriocin Encoding Operon.

Figure 3A:
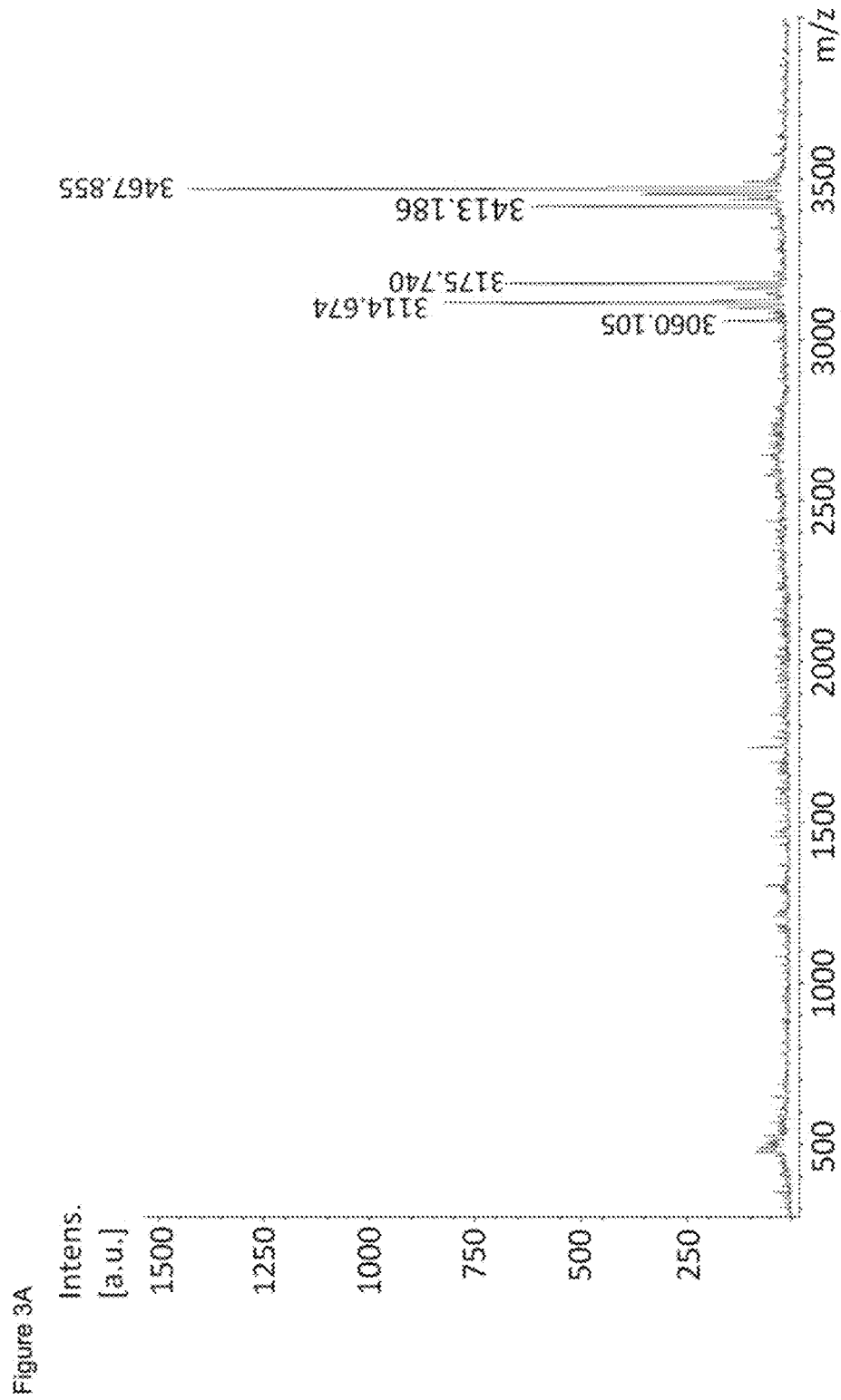
FIG. 3 shows the results of MS of highly active fractions of Garvicin KS bacteriocin after the first RFC, a) from the first peak and b) from the second peak.
Figure 3B:
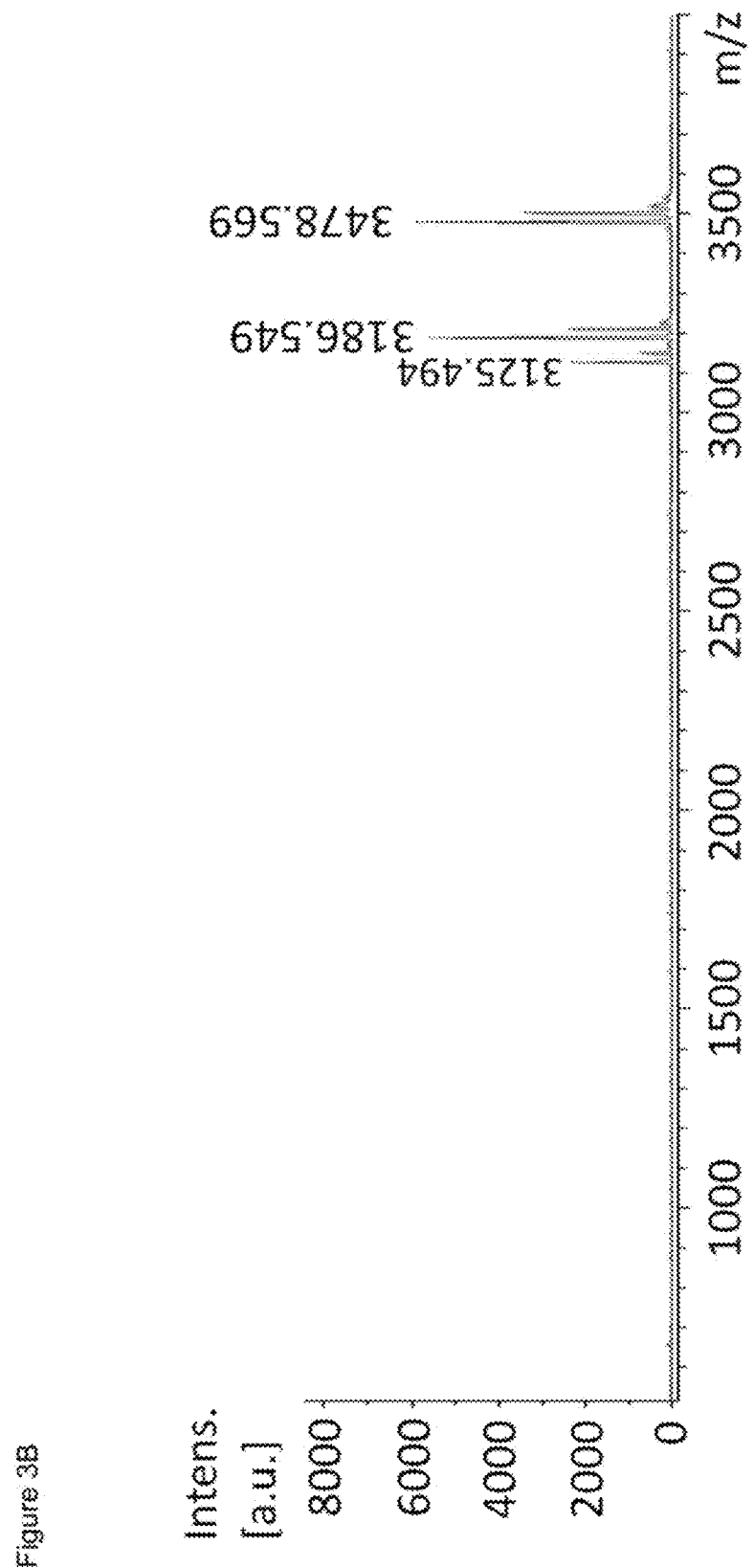

Based on the amino acid sequence obtained, we searched for the corresponding gene in the bacterial genome of the producer. An open reading frame (ORF) was found to encode a peptide of 34 amino acid residues, of which the first 20 amino acids perfectly matched the peptide sequence obtained by the Edman degradation (FIG. 5 a). However, the theoretical monoisotopic mass of the gene-derived peptide sequence was 3450.9 Da, which is 29 Da less than the mass determined by the MS analysis of the purified peptide (3479.9 Da). Further analysis of the genome DNA sequence at the flanking regions revealed two additional small orffs that encoded putative peptides with high sequence similarity to the aforementioned ORF. The additional two peptides were of 34 and 32 amino acids, with theoretical monoisotopic masses of 3158.8 and 3097.7 Da, respectively (FIG. 5 a). Interestingly, these two masses are also about 29 Da less than the two of the predominant peaks (3186.5 and 3125.5 Da) observed in the MS analysis of Peak 2 (FIG. 3 b). The difference in peptide masses obtained in MS and masses from DNA sequence is explained by formylation of the first methionine residues of the peptides during translation, which adds 29 Da to the masses. Many, if not all leaderless bacteriocins have formylmethionine at their N-terminals, a feature that distinguishes these molecules from the leader processed bacteriocins (Liu et al., 2011, J. Agric. Food Chem., 59, p 5602-5608). The three putative bacteriocin-like orfs were named GarKosABC in the order, as they are present in the DNA. At this stage, we combined fractions that constitute all three peptides and we observed a strong synergistic increase in antibacterial activity.

Restoration of the Bacterocin Activity with Chemically Synthesized Peptides.

The three identified peptides termed GarKosA, GarKosB and GarKosC were chemically synthesized and tested for antimicrobial activity. The antimicrobial activity of the individual peptides was assessed against $L.$ $lactis$ IL1403 (Table 6). Among the peptides GarKosA was the most active (MIC=360 nM) while KosC showed low activity (MIC=6 μM) and KosB had no measurable activity at the highest concentration tested (12 μM). When the three peptides (GarKosA, B and C) were combined at equal molar concentrations, the MIC value was determined as 12 nM. The activity increased by 30-fold compared to the most potent single peptide (GarKosA). Combinations of any two peptides did not show any increased antimicrobial activity compared to the activity of the individual peptides (data not shown).

bacteriocins against $L.$ $lactis$ IL1403 showed that each was highly active only when its peptides were mixed together and GarvKos had better antimicrobial activity compared to CereinH, CereinV, CereinX and Aureocin A70. GarvKos was also most active against other bacterial species (Tables 6 and 7).

Comparison of Bacteriocin Operons.

DNA sequences of CerH, CerV, CerX and AurA70 operons, were taken from NCBI databases (accession numbers AHDX01000055.1, AHFF01000058.1, AHCW01000073.1 and AF241888.2 respectively). The operons share significant similarity, particularly for the Cereins (FIG. 5 b). The integrases of CerH and CerX were 93% identical. The same level of identity was observed between the mercury resistance proteins of CerV and CerX operons. Cro/CI family proteins of CerX and CerH were 100% identical and shared a lower identify, 62% identity, with the AurA70 Cro/CI protein. In addition to bacteriocin structural genes, putative bacteriocin ABC transporter genes were found in each operon. These proteins share homology with GarKos ABC transporter (579 aa) over their entire length, with a score varying from 31 to 36 identity. Highest identity (93%) was found between CerX and CerH putative ABC transporters. It is also interesting to note that all the transporters, except for GarKos ABC transporter, were on the opposite to bacteriocins DNA strand. Moreover, in the GarKos, CerH and CerX operons small (150-156 aa) proteins were found which share high similarity with the AurA70 immunity protein (Coelho et al., 2014, Res. Microbiol., 165, p 50-59). They are predicted to have four transmembrane helices.

CereinH—Three or Four Peptide Bacteriocin?

CereinH was expected to consist of three peptides (NCBI accession numbers AHDX01000055.1) but an additional ORF, coding a small (26 aa) peptide MAKIGKWVVK-GAAGYLGWEIGEGIWK (SEQ ID NO:4) was found and named CerH-A. Surprisingly, unlike in the other bacteriocins, CerH-A and CerH-B are very similar not only at their

TABLE 6

Activities of single peptides and their combinations against $L.$ $lactis$ IL1403

| Peptide | Kos A | Kos B | Kos C | CerH A | CerH B | CerH C | CerH D | SA70 A | SA70 B | SA70 C | SA70 D | CerV A | CerV B | CerV C |
|---|---|---|---|---|---|---|---|---|---|---|---|---|---|---|
| MIC | >12 μM | 360 nM | 6 μM | >2.5 μM | 2.5 μM | >2.5 μM | 2.5 μM | >6 μM | >6 μM | >6 μM | 2 μM | 2 μM | >6 μM | >6 μM |
| MICmix | | 12 nM | | | 40 nM | | | | 200 nM | | | | 200 nM | |

Bioinformatics Search for Related Antimicrobial Peptides in Bacterial Genome Sequences.

By using the peptide sequences of GarKos we performed a BLAST search in the bacterial genome data banks. Three homologous putative leaderless bacteriocins were identified (FIG. 6). The putative bacteriocins were apparently made up of multiple peptides. These three putative bacteriocins were identified in the different genomes of $Bacillus$ $cereus$ comprised of three and four peptides, and they were all obtained from unannotated open reading frames. A less closely related bacteriocin was also identified, namely a four-peptide bacteriocin Aureocin A70 produced by $Staphylococcus$ $aureus$ (Netz et al., 2001, J. Mol. Biol., 311, p 939-949).

All putative $B.$ $cereus$ bacteriocins, were chemically synthesized and shown to display antimicrobial activity (FIG. 6, Tables 6 and 7). It was also found that the new bacteriocin CereinX which was expected to have only two peptides in fact consisted of three (NCBI accession number AHCQ01000123.1) (FIG. 6). Testing the activity of those N-termini but also at their C-termini (FIG. 6). Investigations were conducted to establish if antimicrobial activity was possible with only one of those two peptides added to CerHC and CerHD. It was observed that the resulting three peptide mixtures were equally active against related bacterial species but against bacteria from different genera the mixture with the longer peptide, CerHB, was 4-8 times more efficient (data not shown) and even more efficient than the mixture of all four peptides.

TABLE 7

MIC values of GarKos, Cerein H and Aureocin A70 against four different bacterial species

| | GarKos | CerH | CerV | AurA70 |
|---|---|---|---|---|
| $B.$ $cereus$ LMGT 2805 | 80 | 160 | 160 | 340 |
| $L.$ $garvieae$ LMGT 1356 | 40 | 160 | | 640 |
| $L.$ $monocytogenes$ LMGT 319 | 80 | 160 | | 320 |

TABLE 7-continued

MIC values of GarKos, Cerein H and Aureocin A70
against four different bacterial species

|  | GarKos | CerH | CerV | AurA70 |
|---|---|---|---|---|
| E. faecium LMGT 2763 | 80 | 160 |  | 1270 |
| P. pentosacens LMG 2001 | 40 | 80 | 230 | 160 |
| L. salivarius LMG 2787 2787PL | 160 | 320 |  |  |

Peptides with Similar Sequence from Different Bacteriocins can Substitute Each Other in Bacteriocin Assays.

As seen in FIG. 6, peptides from the different bacteriocins exhibit strong sequence homology that is especially pronounced at their N- and C-terminal parts. Sequence related peptides from different bacteriocins were exchanged to see if the antimicrobial activity was maintained or changed in any way. The GarKosA and GarKosB peptides can replace similar peptides from CereinH and the hybrid composition is even twice as active as the indigenous peptides (Table 8). Other peptide replacements led to decreases in antibacterial activity from 2 to 64 fold. Generally, GarKos peptides could replace CereinH and Aureocin A70 peptides with the resulting mixture having similar or even enhanced antimicrobial activity but single peptides from CereinH and A70 similar in sequence to GarKos peptides when used to replace their counterparts resulted in decreased activity (up to 64 fold) of the resulting mixture (Table 8).

TABLE 8

Substitution of similar peptides from different bacteriocins and comparison
of the resulting mixtures activities with WT of bacteriocins

| Substitution in GarKos | Activity (fold) | Substitution in CerH | Activity (fold) | Substitution in CerV | Activity (fold) | Substitution in A70 | Activity (fold) |
|---|---|---|---|---|---|---|---|
| kA + kC + hC | −8 | kA + hC + hD | +2 | vA + xC + vC | 0 | aA + kB + aC + aD | −2 |
| kA + kC + aB | −8 | hA + hB + kB + hD | +2 |  |  | aA + hC + aC + aD | −2 |
| kB + kC + hA | −64 | hA + hB + aB + hD | −2 |  |  | aA + xC + aC + aD | −2 |
| kA + kB + aA | −16 | hA + hB + xC + hD | 0 |  |  | aA + vB + aC + aD | −4 |
| kA + xC + kC | −4 | hA + hB + vB + hD | 0 |  |  |  |  |
| kA + vB + kC | −4 | vC + hC + hD | −4 |  |  |  |  |
| kB + kC + vC | −8 | hA + hB + hC + vA | −4 |  |  |  |  |
| kA + kB + vA | −4 |  |  |  |  |  |  |
| kA + xB + kC | −64 |  |  |  |  |  |  | k = GarKos, h = CerH, v = CerV, x = CerX and a = AurA70
−Decreased activity (fold) in comparison with the WT bacteriocin
+Increased activity (fold) in comparison with the WT bacteriocin Similar results were obtained with substitution assays in CereinV and CereinX bacteriocins (data not shown).

Example 3: Determining the Role of Tryptophan Residues in Garvicin KS's Activity Materials and Methods Production of Variant Garvicin KS Peptides by Replacing the Tryptophan Residues in GarA with Alanine (SEQ ID NO:1)

The three tryptophan residues in GarA were replaced one by one with alanine (Table 9). Antibacterial activity was tested when used in combination with the other peptides of Garvicin KS.

TABLE 9

Garvicin KS peptides and mutant peptides

| Garvicin KS | GarA | MGAIIKAGAKIVGKGVLGGGASWLGWNVGEKIWK |
|---|---|---|
|  | GarB | MGAIIKAGAKIIGKGLLGGAAGGATYGGLKKIFG |
|  | GarC | MGAIIKAGAKIVGKGALTGGGVWLAEKLFGGK |
| Mutant peptides | GarA-23A | MGAIIKAGAKIVGKGVLGGGASLGWN-VGEKIWK (SEQ ID NO. 32) |
|  | GarA-26A | MGAIIKAGAKIVGKGVLGGGASWLGN-VGEKIWK (SEQ ID NO: 33) |
|  | GarA-33A | MGAIIKAGAKIVGKGVLGGGASWLGWN-VGEKIK (SEQ ID NO: 34) |

Results

The mutants showed not only improved synthesis with high purity (95% or more), but differences in activity. GarA-23A and GarA-33A exhibited reduced activity 2-4 times lower than the wildtype peptide (GarA) while GarA-26A showed no antibacterial activity. These results indicate the importance of tryptophan GarA-26W for garvicin KS activity.

Like GarA peptide, the other bacteriocin peptides from the garvicin KS group contain a similar series of three tryptophan residues in their sequences: these are CehB, CevC, CexA, as shown below.

```
CehB    MGALVK-GGLKLIG----GTAASWLGWEAGER-VWK-30

CevC    MGAVVK-GGLKIIG----GTAASWLGWEAGTR-IWK-30

GarA    MGAIIK-AGAKIVGKGVLGGGASWLGWNVGEK-IWK-34

CehA    MAK--I-GKWVVKG------AAGYLGWEIGEG-IWK-26

CexA    MGKK-I-GKWIITG------AAGWAGWEIGEG-IWK-27

A70A    MGKLAI-KAGKIIG----GGIASALGWAAGEKAVGK-31
```

Each of the family members exhibit at least one peptide with at least one tryptophan residue corresponding to the GarA-26W. Further some other peptides also appear to have one or two of these conserved tryptophan residues in their sequence: CehA and A70A. Importantly, all these peptides contain the same tryptophan residue corresponding to GarA-26W. A tryptophan is not found at this position in Aureocin A70.

The invention claimed is:

1. A multi-peptide composition comprising at least:
   a) a peptide comprising the sequence as set forth in SEQ ID NO:1 (GarA) or a sequence with at least 80% sequence identity thereto;
   b) a peptide comprising the sequence as set forth in SEQ ID NO:2 (GarB) or a sequence with at least 80% sequence identity thereto; and
   c) a peptide comprising the sequence as set forth in SEQ ID NO:3 (GarC) or a sequence with at least 80% sequence identity thereto;
   wherein the sequence as set forth in SEQ ID NO:1 or said sequence with at least 80% sequence identity thereto comprises at least two tryptophan residues, and
   wherein each of said peptides is from 25 to 40 amino acids in length and said composition has antibacterial activity.

2. A composition as claimed in claim 1 wherein said sequence identity in any one of a), b) and/or c) is at least 90 or 95% sequence identity.

3. A composition as claimed in claim 1 wherein at least one of the peptides in said composition has the consensus sequence:

$X^1Y^1GWY^2Y^3GY^4Y^5Y^6X^2K$, wherein $X^1$ and $X^2$ may each be any amino acid, with the proviso that at least one of $X^1$ and $X^2$ is a tryptophan residue; and each Y may be any amino acid.

4. A composition as claimed in claim 1 wherein each of said peptides is from 30 to 35 amino acids in length.

5. A composition as claimed in claim 1, wherein said composition comprises a peptide with at least 80% sequence identity to SEQ. ID. NO: 1, 2 or 3.

6. A composition as claimed in claim 1, wherein said composition has antibacterial activity against at least one bacteria selected from the genera *Bacillus, Streptococcus, Listeria, Enterococcus, Staphylococcus, Acinetobacter* and *Paenibacillus*.

7. A composition as claimed in claim 1 wherein the peptides that are present are provided in the ratio 0.5-2:0.5-2:0.5-2 when three peptides are present and 0.5-2:0.5-2:0.5-2 when four peptides are present.

8. A composition as claimed in claim 1 wherein said composition further comprises an additional antibacterial agent.

9. A pharmaceutical composition comprising a composition as defined in claim 1 and a pharmaceutically acceptable diluent or carrier.

10. A probiotic composition comprising a composition as defined in claim 1, wherein said composition additionally comprises at least one probiotic microorganism.

11. A product comprising a composition as defined in claim 1 selected from the list consisting of:
   i) a food product and said composition;
   ii) an item covered, impregnated, or coated with said composition; and
   iii) a personal health care product comprising said composition.

12. The composition as claimed in claim 3, wherein the consensus sequence satisfies one or more of the following:
   a) $X^1$ and $X^2$ are both tryptophan residues;
   b) $Y^1$ is an alanine or leucine residue;
   c) $Y^2$ is a glutamic acid residue;
   d) $Y^3$ is a hydrophobic amino acid residue selected from alanine, valine, leucine, isoleucine, proline, or methionine;
   e) $Y^4$ is a glutamic acid residue; and
   f) $Y^6$ is an isoleucine residue.

13. The composition as claimed in claim 12, wherein $Y^3$ is alanine, valine or isoleucine.

14. A composition as claimed in claim 4, wherein each peptide is cationic.

15. A composition as claimed in claim 6, wherein said composition has antibacterial activity against at least one bacteria selected from the species *Bacillus cereus, Listeria monocytogenes, Listeria innocua, Listeria grayi, Listeria seelingeri, Streptococcus thermophylus, Streptococcus agalactia, Streptococcus pneumonia, Streptococcus salivarius, Enterococcus faecalis, Enterococcus faecium, Staphylococcus aureus, Acinetobacter baumanii, Acinetobacter nosocomialis* and *Paenibacillus larvae*.

16. A composition as claimed in claim 15, wherein said at least one bacteria is selected from Methicillin-resistant *Staphylococcus aureus* (MRSA), antimicrobial resistant (AMR) *Acinetobacter baumanii*, Vancomycin-resistant *Entercocci* (VRE) and antibiotic-resistant strains of *Listeria monocytogenes*.

17. A composition as claimed in claim 6, wherein said composition has antibacterial activity against at least one bacteria from each of the genera *Bacillus, Streptococcus, Listeria, Enterococcus, Staphylococcus, Acinetobacter* and *Paenibacillus*.

18. A composition as claimed in claim 7, wherein said peptides are provided in equimolar amounts.

19. A product as claimed in claim 11, wherein said item is a medical device, instrument, implement or equipment, a prosthetic or material, tissue or wound dressing.

20. A product as claimed in claim 11, wherein said personal health care product is toothpaste, mouthwash, skin cream, lotion or spray.

* * * * *

SEQUENCE LISTING

<160> NUMBER OF SEQ ID NOS: 34

<210> SEQ ID NO 1
<211> LENGTH: 34
<212> TYPE: PRT
<213> ORGANISM: Lactococcus garvieae

<400> SEQUENCE: 1

Met Gly Ala Ile Ile Lys Ala Gly Ala Lys Ile Val Gly Lys Gly Val
1               5                   10                  15

Leu Gly Gly Gly Ala Ser Trp Leu Gly Trp Asn Val Gly Glu Lys Ile
            20                  25                  30

Trp Lys

<210> SEQ ID NO 2
<211> LENGTH: 34
<212> TYPE: PRT
<213> ORGANISM: Lactococcus garvieae

<400> SEQUENCE: 2

Met Gly Ala Ile Ile Lys Ala Gly Ala Lys Ile Ile Gly Lys Gly Leu
1               5                   10                  15

Leu Gly Gly Ala Ala Gly Gly Ala Thr Tyr Gly Gly Leu Lys Lys Ile
            20                  25                  30

Phe Gly

<210> SEQ ID NO 3
<211> LENGTH: 32
<212> TYPE: PRT
<213> ORGANISM: Lactococcus garvieae

<400> SEQUENCE: 3

Met Gly Ala Ile Ile Lys Ala Gly Ala Lys Ile Val Gly Lys Gly Ala
1               5                   10                  15

Leu Thr Gly Gly Gly Val Trp Leu Ala Glu Lys Leu Phe Gly Gly Lys
            20                  25                  30

<210> SEQ ID NO 4
<211> LENGTH: 26
<212> TYPE: PRT
<213> ORGANISM: Bacillus cereus

<400> SEQUENCE: 4

Met Ala Lys Ile Gly Lys Trp Val Val Lys Gly Ala Ala Gly Tyr Leu
1               5                   10                  15

Gly Trp Glu Ile Gly Glu Gly Ile Trp Lys
            20                  25

<210> SEQ ID NO 5
<211> LENGTH: 30
<212> TYPE: PRT
<213> ORGANISM: Bacillus cereus

<400> SEQUENCE: 5

Met Gly Ala Leu Val Lys Gly Gly Leu Lys Leu Ile Gly Gly Thr Ala
1               5                   10                  15

Ala Ser Trp Leu Gly Trp Glu Ala Gly Glu Arg Val Trp Lys
            20                  25                  30

<210> SEQ ID NO 6
<211> LENGTH: 30

<212> TYPE: PRT
<213> ORGANISM: Bacillus cereus

<400> SEQUENCE: 6

Met Gly Ala Ile Ile Lys Gly Gly Leu Lys Leu Val Gly Gly Gly Ala
1 5 10 15

Ala Gly Gly Phe Thr Tyr Gly Gly Leu Lys Lys Ile Phe Gly
20 25 30

<210> SEQ ID NO 7
<211> LENGTH: 30
<212> TYPE: PRT
<213> ORGANISM: Bacillus cereus

<400> SEQUENCE: 7

Met Gly Ala Ile Ile Lys Gly Ala Ala Lys Val Leu Gly Lys Gly Ala
1 5 10 15

Ala Thr Gly Gly Val Ile Tyr Gly Leu Glu Lys Leu Phe Arg
20 25 30

<210> SEQ ID NO 8
<211> LENGTH: 30
<212> TYPE: PRT
<213> ORGANISM: Bacillus cereus

<400> SEQUENCE: 8

Met Gly Ala Val Val Lys Gly Gly Leu Lys Ile Ile Gly Gly Thr Ala
1 5 10 15

Ala Ser Trp Leu Gly Trp Glu Ala Gly Thr Arg Ile Trp Lys
20 25 30

<210> SEQ ID NO 9
<211> LENGTH: 30
<212> TYPE: PRT
<213> ORGANISM: Bacillus cereus

<400> SEQUENCE: 9

Met Gly Ala Ala Val Lys Met Leu Gly Lys Ala Phe Ala Gly Gly Val
1 5 10 15

Ala Gly Gly Ala Thr Tyr Gly Gly Leu Lys Lys Ile Phe Gly
20 25 30

<210> SEQ ID NO 10
<211> LENGTH: 31
<212> TYPE: PRT
<213> ORGANISM: Bacillus cereus

<400> SEQUENCE: 10

Met Gly Ala Val Val Lys Gly Ala Leu Lys Ile Ile Gly Gly Gly Ala
1 5 10 15

Ala Ser Gly Gly Ala Val Tyr Gly Leu Glu Arg Ile Phe Gly Arg
20 25 30

<210> SEQ ID NO 11
<211> LENGTH: 27
<212> TYPE: PRT
<213> ORGANISM: Bacillus cereus

<400> SEQUENCE: 11

Met Gly Lys Lys Ile Gly Lys Trp Ile Ile Thr Gly Ala Ala Gly Trp
1 5 10 15

Ala Gly Trp Glu Ile Gly Glu Gly Ile Trp Lys

<210> SEQ ID NO 12
<211> LENGTH: 30
<212> TYPE: PRT
<213> ORGANISM: Bacillus cereus

<400> SEQUENCE: 12

Met Gly Ala Leu Phe Lys Ala Ala Leu Lys Ala Ala Gly Gly Ala
1               5                   10                  15
Ala Gly Gly Ala Thr Tyr Gly Gly Leu Lys His Phe Phe Gly
                20                  25                  30

<210> SEQ ID NO 13
<211> LENGTH: 29
<212> TYPE: PRT
<213> ORGANISM: Bacillus cereus

<400> SEQUENCE: 13

Met Lys Tyr Leu Gly Thr Leu Ile Lys Gly Ala Ala Gly Gly Ala Gly
1               5                   10                  15
Ala Tyr Val Gly Glu Lys Ile Tyr Asn Trp Tyr Lys Asn
                20                  25

<210> SEQ ID NO 14
<211> LENGTH: 105
<212> TYPE: DNA
<213> ORGANISM: Lactococcus garvieae

<400> SEQUENCE: 14
atgggtgcaa ttatcaaagc aggtgctaaa atcgttggaa aaggcgtatt aggaggcgga      60
gcttcttggc ttggatggaa cgtcggcgaa aaatttgga ataa                      105

<210> SEQ ID NO 15
<211> LENGTH: 105
<212> TYPE: DNA
<213> ORGANISM: Lactococcus garvieae

<400> SEQUENCE: 15
atgggtgcaa ttattaaagc aggtgctaaa atcattggaa aaggcttatt aggggggcgca    60 gctggaggcg ctacttatgg tggcttaaaa aaaatatttg gttaa                    105

<210> SEQ ID NO 16
<211> LENGTH: 99
<212> TYPE: DNA
<213> ORGANISM: Lactococcus garvieae

<400> SEQUENCE: 16
atgggtgcaa ttatcaaagc aggtgctaaa atcgttggaa aaggtgcact aactggtggt     60
ggagtttggc ttgcagaaaa attatttgga ggtaaataa                            99

<210> SEQ ID NO 17
<211> LENGTH: 150
<212> TYPE: PRT
<213> ORGANISM: Lactococcus garvieae

<400> SEQUENCE: 17

Met Leu Tyr Phe Gly Gly Lys Asn Met Lys Lys Ile Asn Asp Glu Arg
1               5                   10                  15
Ile Ile Lys Lys Asp Asn Glu Ile Ile Thr Arg Thr Phe Ile Leu Met
                20                  25                  30

```
Phe Val Leu Ser Leu Phe Tyr Ile Val Leu Phe Asn Lys Val Val Phe
        35                  40                  45

Phe Arg Glu Gln Pro Gln Ala Thr Ile Phe Ser Ile Ile Ile Ile Thr
    50                  55                  60

Thr Val Tyr Phe Ile Phe Asp Ser Phe Ile Ser Lys Thr Leu Phe Val
65                  70                  75                  80

Asn Ile Gln Glu Lys Asn Asp Val Leu Lys Lys Val Ser His Ile Cys
                85                  90                  95

Ser Leu Ile Ile Ala Phe Asp Thr Leu Phe Ile Leu Leu Ser Leu Thr
            100                 105                 110

Lys Lys Ile Asn Ile Asp Leu Asn Leu Asp Thr Ile Ile Val Leu Leu
        115                 120                 125

Ser Leu Asn Ile Phe Leu Phe Ile Ser Tyr Tyr Ala Ile Leu Arg Leu
    130                 135                 140

Trp Val Lys Trp Ile Lys
145                 150

<210> SEQ ID NO 18
<211> LENGTH: 156
<212> TYPE: PRT
<213> ORGANISM: Bacillus cereus

<400> SEQUENCE: 18

Met Glu Lys Leu Lys Asn Trp Phe Ser Leu Ser Thr His Ser Asp Glu
1               5                   10                  15

Arg Ile Gln Gln Ile Glu Met Lys Ile Trp Ala Gln Ser Gly Ile Val
            20                  25                  30

Val Leu Leu Leu Ala Phe Ile Asp Phe Ile Ile Arg Gly Leu Tyr Leu
        35                  40                  45

Gln Arg Pro Phe Leu Glu Trp Ala Ala Thr Leu Ala Ile Ile Ile Cys
    50                  55                  60

Tyr Ile Val Phe Phe Leu Ile Arg Ser Val Leu Ala Gly Val Tyr Glu
65                  70                  75                  80

Thr Asp Ile His Asn Lys Glu Gln Leu Asn Lys Lys Leu Lys Glu Lys
                85                  90                  95

Met Val Asn Thr Phe Ile Phe Cys Phe Val Ala Ile Ser Ile Thr Thr
            100                 105                 110

Tyr Arg Asn Gln Leu Pro Glu Asn Thr Ile Gly Trp Leu Leu Val Ile
        115                 120                 125

Leu Lys Phe Ile Ile Val Phe Ser Leu Ile Phe Gly Ile Gln Tyr Leu
    130                 135                 140

Ile Ala Lys Phe Thr Trp Tyr Lys Asn Asn Lys Asn
145                 150                 155

<210> SEQ ID NO 19
<211> LENGTH: 156
<212> TYPE: PRT
<213> ORGANISM: Bacillus cereus

<400> SEQUENCE: 19

Met Glu Arg Leu Lys Lys Trp Phe Ser Leu Asn Thr His Pro Asp Glu
1               5                   10                  15

Arg Ile Gln Gln Ile Glu Met Lys Ile Trp Ala Gln Ser Gly Ile Ile
            20                  25                  30

Val Leu Leu Ile Ala Phe Ile Asp Phe Ile Ile Arg Gly Ala Tyr Leu
        35                  40                  45
```

```
His Arg Pro Phe Leu Glu Trp Ala Ala Ser Leu Ala Ile Ile Ile Phe
        50                  55                  60

Tyr Met Ile Phe Phe Phe Ile Lys Ser Ile Leu Thr Gly Ile Tyr Glu
65                  70                  75                  80

Thr Asp Ile Asn Asn Lys Glu Gln Leu Asn Glu Lys Leu Lys Glu Lys
                85                  90                  95

Met Ser Asn Thr Leu Ile Phe Cys Phe Val Ala Ile Gly Thr Thr Thr
                100                 105                 110

Tyr Lys Tyr Asn Leu Pro Glu Asp Phe Ile Gly Trp Leu Ser Val Ile
            115                 120                 125

Ala Arg Phe Ile Ile Leu Phe Ala Phe Leu Phe Gly Ile Gln Tyr Leu
        130                 135                 140

Ile Thr Lys Tyr Thr Trp Tyr Lys Asn Asn Lys Asn
145                 150                 155

<210> SEQ ID NO 20
<211> LENGTH: 579
<212> TYPE: PRT
<213> ORGANISM: Lactococcus garvieae

<400> SEQUENCE: 20

Met Lys Arg Asn Ile Lys Asn Ile Ile Asn Ile Val Asn Ile Lys Lys
1               5                   10                  15

Arg Thr Leu Phe Leu Gly Ile Ile Phe Ser Leu Leu Gly Thr Leu Ala
            20                  25                  30

Ser Leu Ser Leu Pro Leu Ile Leu Lys Asn Ile Asp Ser Leu Ile
        35                  40                  45

Asn Lys Asn Phe Asn Ile Tyr Leu Val Ile Phe Leu Cys Ser Leu Ala
    50                  55                  60

Ile Phe Asp Ile Ile Phe Ala Gly Met Ser Ile Tyr Leu Leu Ser Lys
65                  70                  75                  80

Val Gly Glu Glu Val Leu Gly Leu Arg Lys Lys Ile Trp Leu Lys
                85                  90                  95

Ile Leu Asn Ser Lys Ser Asp Phe Phe Glu His Asn Ser Gln Gly Glu
                100                 105                 110

Leu Val Ser Arg Ile Met Asp Asp Thr Lys Lys Leu Met Asp Ile Phe
            115                 120                 125

Ser Thr Asp Ala Ser Asp Phe Val Thr Gly Leu Phe Thr Leu Ile Gly
        130                 135                 140

Thr Val Val Ile Leu Met Thr Ile Asp Pro Leu Leu Thr Ala Leu Ile
145                 150                 155                 160

Phe Ile Ser Ile Pro Ile Ile Val Leu Ile Val Ile Pro Leu Gly Lys
                165                 170                 175

Ser Leu Tyr Lys Phe Ser Ile Lys Ile Gln Glu Asn Asn Ala Ile Ala
            180                 185                 190

Ser Glu Tyr Ile Val Asp Arg Val Ser Asn Ile Lys Leu Ile Lys Met
        195                 200                 205

Ser Asn Thr Leu Phe Glu Glu Leu Tyr Ser Gly Ile Glu Leu Phe Arg
    210                 215                 220

Asn Ile Tyr Lys Ile Asn Met Asn Arg Asn Lys Ile Gln Ser Val Val
225                 230                 235                 240

Leu Pro Ile Ile Thr Leu Thr Ile Thr Ser Thr Ile Ile Gly Ile Val
                245                 250                 255

Phe Phe Gly Ala Phe Arg Val Ile Asn Gly Ala Leu Ser Pro Gly Ala
```

```
            260                 265                 270
Leu Phe Ala Phe Val Val Tyr Ile Val Gln Val Thr Gly Pro Leu Ile
        275                 280                 285

Thr Ile Leu Thr Phe Trp Asn Lys Leu Asn Thr Ala Ile Gly Ser Ser
    290                 295                 300

Asp Arg Ile Ile Asp Ile Leu Asn Tyr Leu Glu Asp Asn Ile Glu
305                 310                 315                 320

Asn Ile Glu Lys Asp Ser Asn Tyr Ser Ile Asp Tyr Leu Ala Leu Asp
                325                 330                 335

His Ile Asn Phe Ser Ile Asp Asp Thr Lys Ile Ile Lys Asp Phe Ser
            340                 345                 350

Tyr Ile Phe Lys Lys Gly Asn Phe Tyr Asn Leu Leu Gly Tyr Ser Gly
        355                 360                 365

Ser Gly Lys Thr Thr Ile Phe Asn Ile Ile Cys Lys Phe Ile Thr Pro
    370                 375                 380

Asp Thr Gly Ser Leu Tyr Thr Asn His Thr Asn Asn Tyr Asn Ile Tyr
385                 390                 395                 400

Ala Trp Arg Glu Asn Ile Ser Tyr Val Ser Gln Asp Ile Ser Ile Ile
                405                 410                 415

Asn Gly Thr Leu Lys Glu Asn Ile Leu Tyr Gly Val Lys Gln Ser Tyr
            420                 425                 430

Ser Asp Glu Phe Leu Leu Ala Leu Leu Gln Glu Ile Gly Leu Lys Lys
        435                 440                 445

Leu Leu Lys Gln Leu Pro Asp Gly Leu Asn Thr Lys Ile Ser Lys Asn
    450                 455                 460

Ser Ser Leu Leu Ser Gly Gly Glu Lys Gln Arg Ile Ala Leu Leu Arg
465                 470                 475                 480

Gly Cys Leu Ser Asp Lys Gln Ile Leu Leu Val Asp Glu Val Ser Ser
                485                 490                 495

Asn Val Asp Ser Lys Asn Asp Phe Arg Ile Tyr Ser Phe Leu Lys Asn
            500                 505                 510

His Asn Asp Asn Lys Ile Ile Ile Met Ile Thr His Lys Leu Ser Asn
        515                 520                 525

Ile Asn Asn Glu Asp Pro Ile Leu Leu Leu Glu Asn Gly Lys Leu Ile
    530                 535                 540

Ala Ser Gly Leu Lys Asn Glu Val Ser Lys Ser Ser Leu Phe Lys
545                 550                 555                 560

Glu Leu Glu Asn Tyr Tyr Arg Gly Asn Ile Asn Asn Glu Tyr Leu Met
                565                 570                 575

Ser Gln Asp

<210> SEQ ID NO 21
<211> LENGTH: 573
<212> TYPE: PRT
<213> ORGANISM: Bacillus cereus

<400> SEQUENCE: 21

Met Gly Lys Asp Lys Asp Val Ser Leu Lys Ala Leu Trp Glu Ile Thr
1               5                   10                  15

Thr Pro P

```
                50              55              60
Leu Leu Leu Ile Val Glu Ile Ser Met Ser Leu Ser Leu Tyr Leu
65                      70              75                  80

Leu Ser Leu Val Gly Gln Arg Val Val Leu Asn Leu Arg Lys Met Ile
                        85              90              95

Trp Arg Lys Ile Leu Asn Leu Lys Val Asp Phe Tyr Ser Lys Asn Gln
                100             105             110

Pro Gly Glu Ile Ile Ser Arg Val Thr Asn Asp Thr Thr Val Thr Met
            115             120             125

Asn Leu Leu Ser Asn Glu Ile Ala Asp Leu Phe Ser Ser Gly Leu Ser
        130             135             140

Met Ile Gly Ala Val Val Ile Leu Phe Leu Leu Asp Val Pro Met Thr
145             150             155             160

Leu Thr Leu Leu Ser Ala Ile Pro Val Thr Leu Phe Ile Val Ile Pro
                165             170             175

Ile Ser Arg Lys Ile Tyr Lys Val Ser Tyr Glu Gln Gln Glu Lys Met
            180             185             190

Ser Glu Phe Thr Ala Leu Leu Ser Gln Val Leu Gly Glu Ile Arg Leu
        195             200             205

Ile Lys Ser Tyr Gly Thr Glu Asp Phe Glu Phe Glu Arg Gly Lys Lys
210             215             220

Lys Ile Glu Glu Leu Tyr Val Asn Gly Met Lys Arg Ala Lys Ile Glu
225             230             235             240

Ser Ile Leu Ile Pro Leu Met Thr Val Ser Ile Thr Leu Ile Ile Val
                245             250             255

Val Val Val Gly Phe Gly Ser Tyr Arg Val Ser Glu Gly Tyr Leu Ser
            260             265             270

Ser Gly Glu Leu Leu Ala Phe Ile Leu Tyr Leu Phe Gln Ile Val Gly
        275             280             285

Pro Val Gly Val Met Ser Arg Phe Ile Thr Ser Val Gln Ser Ala Lys
        290             295             300

Gly Ser Thr Glu Arg Ile Phe Asn Ile Leu Asp Glu Lys Asp Glu Lys
305             310             315             320

Thr Lys Val Asn Phe Leu Glu Glu Pro Ser Phe Gly Ile Leu Glu Leu
                325             330             335

Lys Gly Leu Asn Phe Gly Tyr Gly Glu Lys Ser Ile Phe Glu Asn Ile
            340             345             350

Asn Leu Lys Ile Met Pro Asn Thr Val Thr Ala Leu Val Gly Pro Ser
        355             360             365

Gly Val Gly Lys Thr Thr Leu Phe Tyr Leu Leu Glu Arg Phe Tyr Asp
        370             375             380

Pro Leu Lys Gly Glu Ile Leu Leu Asp Gly Lys Ser His Leu Asp Ile
385             390             395             400

Asp Leu Asp Lys Trp Arg Ala Met Phe Ser Tyr Val Ser Gln Asp Cys
                405             410             415

Pro Ile Leu Ala Gly Thr Ile Arg Glu Asn Ile Thr Tyr Gly Ile Gln
            420             425             430

Arg Glu Val Ser Lys Asp Glu Ile Ile Lys Ala Ser Val Leu Ala Asn
        435             440             445

Cys His Glu Phe Ile Thr Ser Phe Ser Asp Gly Tyr Asn Thr Ile Leu
        450             455             460

Gly Glu Arg Gly Ile Asn Leu Ser Gly Gly Gln Lys Gln Arg Ile Ser
465             470             475             480
```

```
Ile Ala Arg Ala Phe Leu Arg Asp Thr Pro Phe Leu Leu Leu Asp Glu
                485                 490                 495

Ala Thr Ala Asn Leu Asp Thr Asn Ser Glu Asn Met Ile Lys His Ala
            500                 505                 510

Leu Asp Lys Leu Ile Tyr Lys Lys Thr Thr Ile Val Ile Ala His Arg
        515                 520                 525

Ile Ser Thr Ile Gln Asn Ala Asp Gln Ile Ile Val Leu Asp Gln Gly
    530                 535                 540

Glu Ile Ser Gly Phe Gly Thr His Asp Gln Leu Ile Lys Ser Asn Lys
545                 550                 555                 560

Leu Tyr Gln Leu Leu Ser Asn Gln Gln Lys Met Thr Ser
                565                 570

<210> SEQ ID NO 22
<211> LENGTH: 593
<212> TYPE: PRT
<213> ORGANISM: Bacillus cereus

<400> SEQUENCE: 22

Met Leu Arg Phe Thr Glu Arg Phe Lys Glu Tyr Ile Phe Met Lys Lys
1               5                   10                  15

Glu Lys Thr Met Ser Leu Arg Thr Leu Trp Lys Thr Thr Asn Pro Pro
            20                  25                  30

Asn Thr Pro Leu Ile Phe Gly Ile Ile Leu Ser Leu Ile Asn Thr Ser
        35                  40                  45

Cys Ser Leu Val Ile Pro Leu Ile Leu Lys Lys Gln Ile Glu Gln Leu
    50                  55                  60

Asp Asn Gly Phe Ser Tyr Lys Leu Leu Gly Leu Ile Leu Phe Leu Leu
65                  70                  75                  80

Leu Ile Glu Ile Ile Ser Met Gly Ile Ser Leu Tyr Leu Leu Ser Leu
                85                  90                  95

Val Gly Gln Lys Val Val Leu Asn Leu Arg Thr Ile Leu Trp Lys Lys
            100                 105                 110

Ile Leu Asn Leu Lys Val Asp Phe Tyr Asn Lys Asn Gln Pro Gly Glu
        115                 120                 125

Val Ile Ser Arg Val Thr Asn Asp Thr Thr Val Ala Met Asn Leu Leu
    130                 135                 140

Ser Thr Glu Ile Ala Asp Val Leu Ser Gly Val Leu Ser Met Ile Gly
145                 150                 155                 160

Ser Val Ile Ile Leu Phe Ile Leu Asp Val Pro Met Thr Val Thr Leu
                165                 170                 175

Leu Ser Ala Ile Pro Ile Thr Leu Phe Ile Val Ile Pro Ile Ser Lys
            180                 185                 190

Lys Ile Tyr Lys Val Ser Tyr Glu Gln Gln Glu Lys Met Ser Asp Phe
        195                 200                 205

Thr Ala Leu Leu Ser Gln Val Leu Ser Glu Ile Arg Leu Ile Lys Ser
    210                 215                 220

Tyr Asn Thr Glu Asn Tyr Glu Phe Glu Arg Gly Lys Thr Lys Ile Glu
225                 230                 235                 240

Ala Leu Tyr Lys Asn Gly Met Lys Arg Ala Lys Val Glu Ser Ile Leu
                245                 250                 255

Ile Pro Leu Met Thr Val Val Ile Thr Thr Ile Ile Val Val Ile Val
            260                 265                 270

Gly Phe Gly Ser Tyr Arg Val Ser Lys Gly Tyr Ile Ser Ser Gly Glu
```

```
                275                 280                 285
Leu Leu Ala Phe Ile Leu Tyr Leu Phe Gln Ile Val Ala Pro Val Gly
            290                 295                 300
Thr Met Ser Arg Phe Ile Thr Ser Val Gln Ser Thr Lys Gly Ala Thr
305                 310                 315                 320
Glu Arg Ile Phe Asp Ile Leu Asn Lys Lys Glu Lys Glu Lys Glu Ile
                325                 330                 335
Ala Ser Phe Glu Asn Pro Ser Phe Gly Ile Leu Asp Phe Lys Asn Val
                340                 345                 350
Ser Phe Gly Tyr Asp Glu Lys Thr Ile Leu Asn Asn Ile Ser Phe Gln
                355                 360                 365
Val Ile Pro Asn Thr Val Thr Ala Ile Val Gly Pro Ser Gly Val Gly
            370                 375                 380
Lys Thr Thr Leu Phe Tyr Leu Leu Glu Arg Phe Tyr Thr Pro Thr Cys
385                 390                 395                 400
Gly Glu Ile Ser Leu Asn Gly Lys Pro Gln Leu Asn Ile Glu Leu Glu
                405                 410                 415
Lys Trp Arg Ser Met Phe Ser Tyr Val Ser Gln Asp Cys Pro Ile Leu
                420                 425                 430
Val Gly Thr Ile Lys Glu Asn Ile Leu Tyr Gly Ile Gln Arg Lys Val
            435                 440                 445
Ser Glu Glu Glu Ile Ile Lys Val Ser Asn Leu Ala Asn Cys His Asn
            450                 455                 460
Phe Ile Thr Glu Leu Pro Asn Gly Tyr Asp Thr Lys Leu Gly Glu Arg
465                 470                 475                 480
Gly Ile Asn Ile Ser Gly Gly Gln Lys Gln Arg Ile Ala Ile Ala Arg
                485                 490                 495
Ala Leu Leu Arg Asn Ala Pro Phe Leu Leu Leu Asp Glu Ala Thr Ala
            500                 505                 510
Asn Leu Asp Thr Lys Ser Glu Ile Met Ile Lys Glu Ala Met Glu Lys
            515                 520                 525
Leu Ile Tyr Gly Lys Thr Thr Ile Val Ile Ala His Arg Ile Ser Thr
            530                 535                 540
Ile Gln Asn Ala Asp Gln Ile Ile Val Leu Asp Lys Asn Gly Ile Ser
545                 550                 555                 560
Gly Met Gly Thr His Glu Gln Leu Leu Glu Lys Asn Glu Leu Tyr Gln
                565                 570                 575
Asp Leu Ala Asn Gln Asn His Lys Ala Glu Ile Asn Glu Cys Val Lys
            580                 585                 590
Pro

<210> SEQ ID NO 23
<211> LENGTH: 573
<212> TYPE: PRT
<213> ORGANISM: Bacillus cereus

<400> SEQUENCE: 23

Met Glu Lys Asp Lys Asp Val Ser Leu Lys Ala Leu Trp Glu Ile Thr
1               5                   10                  15
Thr Pro Pro Lys Val Thr Leu Phe Trp Gly Val Ile Phe Gly Leu Ile
                20                  25                  30
Asn Ser Gly Cys Ser Leu Ile Ile Pro Leu Ile Leu Lys Glu Gln Ile
            35                  40                  45
Glu Gln Leu Ser Glu Gly Phe Ser Tyr Glu Leu Leu Phe Leu Val Leu
```

-continued

```
                50                  55                  60
Phe Leu Leu Ile Val Glu Ile Ile Ser Met Gly Phe Ser Leu Tyr Leu
 65                  70                  75                  80

Leu Ser Leu Val Gly Gln Arg Val Val Leu Asn Leu Arg Lys Met Ile
                 85                  90                  95

Trp Arg Lys Val Leu Asn Leu Lys Val Asp Phe Tyr Ser Lys Asn Gln
                100                 105                 110

Pro Gly Glu Ile Ile Ser Arg Val Thr Asn Asp Thr Thr Val Thr Met
                115                 120                 125

Asn Leu Leu Ser Ser Glu Ile Ala Asp Leu Leu Ser Gly Val Leu Ser
                130                 135                 140

Met Ile Gly Ala Val Ala Ile Leu Phe Leu Leu Asp Val Pro Met Thr
145                 150                 155                 160

Leu Thr Leu Leu Ser Ala Val Pro Val Thr Leu Phe Ile Val Ile Pro
                165                 170                 175

Ile Ser Lys Lys Ile Tyr Lys Val Ser Tyr Ala Gln Gln Glu Lys Met
                180                 185                 190

Ser Glu Phe Thr Ala Leu Leu Ser Gln Val Leu Gly Glu Ile Arg Leu
                195                 200                 205

Ile Lys Ser Tyr Gly Thr Glu Asp Phe Glu Phe Glu Arg Gly Lys Lys
210                 215                 220

Lys Ile Glu Glu Leu Tyr Val Asn Gly Ile Lys Arg Ala Lys Ile Glu
225                 230                 235                 240

Ser Ile Leu Ile Pro Leu Met Thr Val Ser Ile Thr Leu Ile Ile Val
                245                 250                 255

Val Val Val Gly Phe Gly Ser Tyr Arg Val Ser Glu Gly Tyr Leu Ser
                260                 265                 270

Ser Gly Glu Leu Leu Ala Phe Ile Leu Tyr Leu Phe Gln Ile Val Gly
                275                 280                 285

Pro Val Gly Val Met Ser Arg Phe Ile Thr Asn Val Gln Ser Ala Lys
                290                 295                 300

Gly Ser Thr Glu Arg Ile Phe Asn Ile Leu Asp Glu Lys Asp Glu Lys
305                 310                 315                 320

Asn Lys Gly Asp Phe Leu Glu Glu Pro Ser Phe Gly Ile Leu Glu Phe
                325                 330                 335

Lys Asp Ile Gly Phe Ala Tyr Asp Glu Lys Asn Ile Phe Glu Asn Ile
                340                 345                 350

Asn Leu Lys Ile Met Pro Asn Thr Val Thr Ala Leu Val Gly Pro Ser
                355                 360                 365

Gly Val Gly Lys Thr Thr Leu Phe Tyr Leu Leu Glu Arg Phe Tyr Asp
370                 375                 380

Pro Leu Lys Gly Glu Ile Leu Leu Asp Gly Lys Ser His Leu Asn Ile
385                 390                 395                 400

Asp Leu Asp Lys Trp Arg Ser Met Phe Ser Tyr Val Ser Gln Asp Cys
                405                 410                 415

Pro Ile Leu Val Gly Thr Ile Arg Glu Asn Ile Ile Tyr Gly Ile Gln
                420                 425                 430

Arg Glu Val Ser Glu Asp Glu Ile Ile Lys Ala Ser Ile Leu Ala Asn
                435                 440                 445

Cys His Glu Phe Ile Thr Ser Phe Ser Asp Gly Tyr Asp Thr Val Leu
                450                 455                 460

Gly Glu Arg Gly Ile Asn Leu Ser Gly Gly Gln Lys Gln Arg Ile Ser
465                 470                 475                 480
```

```
Ile Ala Arg Ala Phe Leu Arg Asp Thr Pro Phe Leu Leu Asp Glu
            485                 490                 495

Ala Thr Ala Asn Leu Asp Thr Asn Ser Glu Asn Met Ile Lys His Ala
        500                 505                 510

Leu Asp Asn Leu Ile Tyr Lys Lys Thr Thr Ile Val Ile Ala His Arg
        515                 520                 525

Ile Ser Thr Ile Gln Asn Ala Asp Gln Ile Val Val Leu Asp Gln Gly
        530                 535                 540

Glu Val Ser Gly Phe Gly Thr His Asp Gln Leu Ile Lys Asn Asn Lys
545                 550                 555                 560

Leu Tyr Gln Leu Leu Ser Asn Gln Gln Lys Met Thr Ser
            565                 570
```

<210> SEQ ID NO 24
<211> LENGTH: 19
<212> TYPE: DNA
<213> ORGANISM: Artificial Sequence
<220> FEATURE:
<223> OTHER INFORMATION: 16S rRNA Primer

<400> SEQUENCE: 24
ggttaccttg ttacgactt                                              19

<210> SEQ ID NO 25
<211> LENGTH: 20
<212> TYPE: DNA
<213> ORGANISM: Artificial Sequence
<220> FEATURE:
<223> OTHER INFORMATION: 16S rRNA Primer

<400> SEQUENCE: 25
taacacatgc aagtcgaacg                                             20

<210> SEQ ID NO 26
<211> LENGTH: 15
<212> TYPE: DNA
<213> ORGANISM: Artificial Sequence
<220> FEATURE:
<223> OTHER INFORMATION: (GTG)5 Genetic Fingerprinting Primer

<400> SEQUENCE: 26
gtggtggtgg tggtg                                                  15

<210> SEQ ID NO 27
<211> LENGTH: 153
<212> TYPE: PRT
<213> ORGANISM: Lactococcus lactis

<400> SEQUENCE: 27

```
Met Ser Gln Arg Gln Leu Thr Lys Ser Val Thr Asn Arg Arg Val Ser
1               5                   10                  15

Gly Val Ile Ala Gly Ile Ala Glu Tyr Phe Gly Leu Gly Arg Asp Val
            20                  25                  30

Val Thr Ile Leu Arg Ile Leu Phe Val Val Leu Ala Phe Gly Ser Trp
        35                  40                  45

Gly Gly Leu Ile Pro Leu Tyr Phe Val Ala Ser Trp Ile Ile Pro Ser
    50                  55                  60

Ala Arg Pro Arg Asn Tyr Tyr Asp Asp Ser Glu Asp Tyr Gln Glu
65                  70                  75                  80

Lys Trp Asn Arg Lys Ala Gln His Phe Asp Glu Lys Met Asp Arg Trp
```

```
                    85                  90                  95

Ser Glu Arg Tyr Ser Asp Lys Met Asn Asn Trp Ala Arg Arg Tyr Glu
            100                 105                 110

Asp Lys Gly Arg Gln Asn Gln Gln Asp Ser Asn Gln Trp Gly Asn Pro
        115                 120                 125

Trp Asp Glu Pro Lys Ser Arg Lys Thr Lys Glu Ala Gln Pro Val Glu
    130                 135                 140

Lys Glu Lys Glu Asp Asp Trp Ser Asp
145                 150

<210> SEQ ID NO 28
<211> LENGTH: 31
<212> TYPE: PRT
<213> ORGANISM: Staphylococcus aureus

<400> SEQUENCE: 28

Met Gly Lys Leu Ala Ile Lys Ala Gly Lys Ile Ile Gly Gly Gly Ile
1               5                   10                  15

Ala Ser Ala Leu Gly Trp Ala Ala Gly Glu Lys Ala Val Gly Lys
            20                  25                  30

<210> SEQ ID NO 29
<211> LENGTH: 30
<212> TYPE: PRT
<213> ORGANISM: Staphylococcus aureus

<400> SEQUENCE: 29

Met Gly Ala Val Ala Lys Phe Leu Gly Lys Ala Ala Leu Gly Gly Ala
1               5                   10                  15

Ala Gly Gly Ala Thr Tyr Ala Gly Leu Lys Lys Ile Phe Gly
            20                  25                  30

<210> SEQ ID NO 30
<211> LENGTH: 31
<212> TYPE: PRT
<213> ORGANISM: Staphylococcus aureus

<400> SEQUENCE: 30

Met Gly Ala Leu Ile Lys Thr Gly Ala Lys Ile Ile Gly Ser Gly Ala
1               5                   10                  15

Ala Gly Gly Leu Gly Thr Tyr Ile Gly His Lys Ile Leu Gly Lys
            20                  25                  30

<210> SEQ ID NO 31
<211> LENGTH: 31
<212> TYPE: PRT
<213> ORGANISM: Staphylococcus aureus

<400> SEQUENCE: 31

Met Gly Ala Val Ile Lys Val Gly Ala Lys Val Ile Gly Trp Gly Ala
1               5                   10                  15

Ala Ser Gly Ala Gly Leu Tyr Gly Leu Glu Lys Ile Leu Lys Lys
            20                  25                  30

<210> SEQ ID NO 32
<211> LENGTH: 34
<212> TYPE: PRT
<213> ORGANISM: Artificial Sequence
<220> FEATURE:
<223> OTHER INFORMATION: Altered Sequence of GarA from Lactococcus
      garvieae with W23A Mutation
```

```
<400> SEQUENCE: 32

Met Gly Ala Ile Ile Lys Ala Gly Ala Lys Ile Val Gly Lys Gly Val
1               5                   10                  15

Leu Gly Gly Gly Ala Ser Ala Leu Gly Trp Asn Val Gly Glu Lys Ile
            20                  25                  30

Trp Lys

<210> SEQ ID NO 33
<211> LENGTH: 34
<212> TYPE: PRT
<213> ORGANISM: Artificial Sequence
<220> FEATURE:
<223> OTHER INFORMATION: Altered Sequence of GarA from Lactococcus
      garvieae with W26A Mutation

<400> SEQUENCE: 33

Met Gly Ala Ile Ile Lys Ala Gly Ala Lys Ile Val Gly Lys Gly Val
1               5                   10                  15

Leu Gly Gly Gly Ala Ser Trp Leu Gly Ala Asn Val Gly Glu Lys Ile
            20                  25                  30

Trp Lys

<210> SEQ ID NO 34
<211> LENGTH: 34
<212> TYPE: PRT
<213> ORGANISM: Artificial Sequence
<220> FEATURE:
<223> OTHER INFORMATION: Altered Sequence of GarA from Lactococcus
      garvieae with W33A Mutation

<400> SEQUENCE: 34

Met Gly Ala Ile Ile Lys Ala Gly Ala Lys Ile Val Gly Lys Gly Val
1               5                   10                  15

Leu Gly Gly Gly Ala Ser Trp Leu Gly Trp Asn Val Gly Glu Lys Ile
            20                  25                  30

Ala Lys
```